(12) United States Patent
Eidenschink

(10) Patent No.: US 7,744,619 B2
(45) Date of Patent: Jun. 29, 2010

(54) ROTATABLE CATHETER ASSEMBLY

(75) Inventor: Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1270 days.

(21) Appl. No.: 10/785,449

(22) Filed: Feb. 24, 2004

(65) Prior Publication Data

US 2005/0187602 A1   Aug. 25, 2005

(51) Int. Cl.
*A61M 29/00* (2006.01)
(52) U.S. Cl. .................................... 606/194; 604/96.01
(58) Field of Classification Search ................. 606/191, 606/194, 195, 192, 198; 600/470; 604/96.01, 604/99.01–99.04, 102.01, 103, 104, 915, 604/916, 920, 921
See application file for complete search history.

(56) References Cited

U.S. PATENT DOCUMENTS

| 4,273,111 | A | 6/1981 | Tsukaya | |
|---|---|---|---|---|
| 4,286,585 | A | 9/1981 | Ogawa | |
| 4,448,195 | A | 5/1984 | Leveen et al. | 128/344 |
| 4,484,585 | A | 11/1984 | Baier | 128/748 |
| 4,499,895 | A | 2/1985 | Takayama | |
| 4,503,842 | A | 3/1985 | Takayama | |
| 4,543,090 | A | 9/1985 | McCoy | |
| 4,601,701 | A | 7/1986 | Mueller, Jr. | 604/83 |
| 4,601,705 | A | 7/1986 | McCoy | |
| 4,753,223 | A | 6/1988 | Bremer | |
| 4,769,005 | A | 9/1988 | Ginsburg et al. | 604/53 |
| 4,776,337 | A | 10/1988 | Palmaz | 128/343 |
| 4,790,624 | A | 12/1988 | Van Hoye et al. | |
| 4,793,359 | A | 12/1988 | Sharrow | |
| 4,830,023 | A | 5/1989 | De Toledo et al. | |
| 4,838,859 | A | 6/1989 | Strassmann | |
| 4,846,573 | A | 7/1989 | Taylor et al. | |
| 4,884,557 | A | 12/1989 | Takehana et al. | |
| 4,899,731 | A | 2/1990 | Takayama et al. | |

(Continued)

FOREIGN PATENT DOCUMENTS

DE   297 01 758   5/1997

(Continued)

OTHER PUBLICATIONS

U.S. Appl. No. 10/375,689, filed Feb. 27, 2003, Eidenschink.

(Continued)

*Primary Examiner*—Michael J Milano
*Assistant Examiner*—Victor X Nguyen
(74) *Attorney, Agent, or Firm*—Crompton, Seager & Tufte, LLC

(57) ABSTRACT

A catheter assembly comprises a catheter shaft, a balloon and a pair of collars. The collars may be fixed or rotatable about a catheter shaft prior to exposure to an electric current. Where the collars are fixed to the shaft, the balloon is rotatable about the collars. When exposed to the electric current the collars expand to engage the waists of the balloon thereby sealing the balloon. Where the collars are rotatable about the shaft, the each waist of the balloon is engaged to a respective collars. When the rotatable collars are exposed to the electric current the collars expand to engage the shaft of the catheter thereby sealing the balloon.

57 Claims, 19 Drawing Sheets

U.S. PATENT DOCUMENTS

| | | | |
|---|---|---|---|
| 4,906,244 A | 3/1990 | Pinchuk et al. | |
| 4,913,141 A | 4/1990 | Hillstead | 606/108 |
| 4,930,494 A | 6/1990 | Takehana et al. | |
| 4,950,239 A | 8/1990 | Gahara et al. | |
| 4,977,886 A | 12/1990 | Takehana et al. | |
| 4,987,314 A | 1/1991 | Gotanda et al. | |
| 4,988,356 A | 1/1991 | Crittenden et al. | |
| 4,994,071 A | 2/1991 | MacGregor | 606/194 |
| 4,998,923 A | 3/1991 | Samson et al. | 606/194 |
| 5,019,085 A | 5/1991 | Hillstead | 606/108 |
| 5,090,956 A | 2/1992 | McCoy | |
| 5,100,933 A | 3/1992 | Tanaka et al. | |
| 5,122,154 A | 6/1992 | Rhodes | 606/198 |
| 5,188,111 A | 2/1993 | Yates et al. | |
| 5,195,984 A | 3/1993 | Schatz | 606/195 |
| 5,209,728 A | 5/1993 | Kraus et al. | |
| 5,219,355 A | 6/1993 | Parodi et al. | 606/191 |
| 5,239,982 A | 8/1993 | Trauthen | |
| 5,250,167 A | 10/1993 | Adolf et al. | |
| 5,268,082 A | 12/1993 | Oguro et al. | |
| 5,290,306 A | 3/1994 | Trotta et al. | |
| 5,316,023 A | 5/1994 | Palmaz et al. | 128/898 |
| 5,318,535 A | 6/1994 | Miraki | |
| 5,337,732 A | 8/1994 | Grundfest et al. | |
| 5,347,987 A | 9/1994 | Feldstein et al. | |
| 5,348,537 A | 9/1994 | Wiesner et al. | |
| 5,368,015 A | 11/1994 | Wilk | |
| 5,389,222 A | 2/1995 | Shahinpoor | |
| 5,396,879 A | 3/1995 | Wilk et al. | |
| 5,397,305 A | 3/1995 | Kawula et al. | 604/96 |
| 5,425,703 A * | 6/1995 | Feiring | 604/21 |
| 5,431,645 A | 7/1995 | Smith et al. | |
| 5,449,343 A | 9/1995 | Samson et al. | |
| 5,477,856 A | 12/1995 | Lundquist | |
| 5,482,029 A | 1/1996 | Sekiguchi et al. | |
| 5,492,121 A | 2/1996 | Lu | |
| 5,492,532 A | 2/1996 | Ryan et al. | |
| 5,500,181 A | 3/1996 | Wang et al. | |
| 5,556,370 A | 9/1996 | Maynard | |
| 5,556,700 A | 9/1996 | Kaneto et al. | |
| 5,609,627 A | 3/1997 | Goicoechea et al. | |
| 5,624,380 A | 4/1997 | Takayama et al. | |
| 5,631,040 A | 5/1997 | Takuchi et al. | |
| 5,632,763 A | 5/1997 | Glastra | |
| 5,643,278 A | 7/1997 | Wijay | |
| 5,645,520 A | 7/1997 | Nakamura et al. | |
| 5,649,923 A | 7/1997 | Gregory et al. | |
| 5,651,366 A | 7/1997 | Liang et al. | |
| 5,662,587 A | 9/1997 | Grundfest et al. | |
| 5,683,345 A | 11/1997 | Waksman et al. | |
| 5,693,015 A | 12/1997 | Walker et al. | |
| 5,697,948 A | 12/1997 | Marin et al. | |
| 5,697,971 A | 12/1997 | Fischell et al. | |
| 5,720,735 A | 2/1998 | Dorros | |
| 5,725,519 A | 3/1998 | Penner et al. | |
| 5,749,825 A | 5/1998 | Fischell et al. | |
| 5,755,734 A | 5/1998 | Richter et al. | |
| 5,755,735 A | 5/1998 | Richter et al. | |
| 5,755,778 A | 5/1998 | Kleshinski | |
| 5,766,013 A | 6/1998 | Vuyk | |
| 5,771,902 A | 6/1998 | Lee et al. | |
| 5,772,669 A | 6/1998 | Vrba | |
| 5,797,952 A | 8/1998 | Klein | |
| 5,824,055 A | 10/1998 | Spiridigliozzi et al. | |
| 5,855,565 A * | 1/1999 | Bar-Cohen et al. | 604/104 |
| 5,857,962 A | 1/1999 | Bracci et al. | |
| 5,873,817 A | 2/1999 | Kokish et al. | |
| 5,873,906 A | 2/1999 | Lau et al. | |
| 5,876,374 A | 3/1999 | Alba et al. | |
| 5,893,868 A | 4/1999 | Hanson et al. | |
| 5,906,591 A | 5/1999 | Dario et al. | |
| 5,906,640 A | 5/1999 | Penn et al. | |
| 5,908,405 A | 6/1999 | Imran et al. | |
| 5,916,146 A | 6/1999 | Allotta et al. | |
| 5,921,995 A | 7/1999 | Kleshinski | |
| 5,935,161 A | 8/1999 | Robinson et al. | |
| 5,941,908 A | 8/1999 | Goldsteen et al. | |
| 5,951,569 A | 9/1999 | Tuckey et al. | |
| 5,957,833 A | 9/1999 | Shan | |
| 5,957,929 A | 9/1999 | Brenneman | |
| 5,961,546 A | 10/1999 | Robinson et al. | |
| 5,961,548 A | 10/1999 | Shmulewitz | |
| 6,010,449 A | 1/2000 | Selmon et al. | |
| 6,013,092 A | 1/2000 | Dehdashtian et al. | |
| 6,017,362 A | 1/2000 | Lau | 623/1 |
| 6,027,460 A | 2/2000 | Shturman | 600/585 |
| 6,033,434 A | 3/2000 | Borghi | 623/1 |
| 6,048,361 A | 4/2000 | Von Oepen | 623/1 |
| 6,056,722 A | 5/2000 | Jayaraman | 604/102 |
| 6,056,775 A | 5/2000 | Borghi et al. | 623/1.16 |
| 6,059,813 A | 5/2000 | Vrba et al. | 606/198 |
| 6,071,234 A | 6/2000 | Takada | |
| 6,071,286 A | 6/2000 | Mawad | 606/108 |
| 6,077,297 A | 6/2000 | Robinson et al. | 623/1.11 |
| 6,090,127 A | 7/2000 | Globerman | 606/194 |
| 6,096,073 A | 8/2000 | Webster et al. | 623/1.16 |
| 6,099,497 A | 8/2000 | Adams et al. | |
| 6,109,852 A | 8/2000 | Shahinpoor et al. | |
| 6,110,191 A | 8/2000 | Dehdashtian et al. | 606/192 |
| 6,117,128 A | 9/2000 | Gregory | |
| 6,117,156 A | 9/2000 | Richter et al. | 606/194 |
| 6,117,296 A | 9/2000 | Thomson | |
| 6,120,522 A | 9/2000 | Vrba et al. | 606/190 |
| 6,132,450 A | 10/2000 | Hanson et al. | 606/198 |
| 6,143,014 A | 11/2000 | Dehdashtian et al. | 606/192 |
| 6,146,415 A | 11/2000 | Fitz | 623/1.11 |
| 6,152,944 A | 11/2000 | Holman et al. | 623/1.11 |
| 6,162,171 A | 12/2000 | Ng et al. | |
| 6,165,195 A | 12/2000 | Wilson et al. | 606/194 |
| 6,165,210 A | 12/2000 | Lau et al. | 623/1.12 |
| 6,187,015 B1 | 2/2001 | Brenneman | 606/108 |
| 6,190,360 B1 | 2/2001 | Iancea et al. | 604/164.09 |
| 6,190,393 B1 | 2/2001 | Bevier et al. | 606/108 |
| 6,210,380 B1 | 4/2001 | Mauch | 604/284 |
| 6,210,431 B1 | 4/2001 | Power | 623/1.11 |
| 6,221,090 B1 | 4/2001 | Wilson | 606/194 |
| 6,221,097 B1 | 4/2001 | Wang et al. | 623/1.11 |
| 6,224,587 B1 | 5/2001 | Gibson | 604/528 |
| 6,238,410 B1 | 5/2001 | Vrba et al. | 606/198 |
| 6,246,914 B1 | 6/2001 | De la Rama et al. | 607/122 |
| 6,249,076 B1 | 6/2001 | Madden et al. | |
| 6,254,593 B1 | 7/2001 | Wilson | 606/1.11 |
| 6,258,052 B1 | 7/2001 | Milo | 604/22 |
| 6,258,073 B1 | 7/2001 | Mauch | 604/284 |
| 6,264,688 B1 | 7/2001 | Herklotz et al. | 623/1.16 |
| 6,280,466 B1 | 8/2001 | Kugler et al. | |
| 6,287,277 B1 | 9/2001 | Yan | 604/96.01 |
| 6,287,330 B1 | 9/2001 | Johansson et al. | 623/1.13 |
| 6,290,668 B1 | 9/2001 | Gregory et al. | |
| 6,290,673 B1 | 9/2001 | Shanley | 604/102.02 |
| 6,299,636 B1 | 10/2001 | Schmitt et al. | 623/1.2 |
| 6,302,906 B1 | 10/2001 | Goicoechea et al. | |
| 6,315,790 B1 * | 11/2001 | Gerberding et al. | 623/1.11 |
| 6,319,275 B1 | 11/2001 | Lashinski et al. | 623/1.11 |
| 6,322,548 B1 | 11/2001 | Payne et al. | 604/500 |
| 6,352,561 B1 | 3/2002 | Leopold et al. | |
| 6,361,544 B1 | 3/2002 | Wilson et al. | 606/194 |
| 6,361,555 B1 | 3/2002 | Wilson | 623/1.11 |
| 6,364,893 B1 | 4/2002 | Sahatjian et al. | 606/194 |
| 6,371,978 B1 | 4/2002 | Wilson | 623/1.11 |
| 6,375,660 B1 | 4/2002 | Fischell et al. | 606/108 |
| 6,375,675 B2 | 4/2002 | Dehdashtian et al. | |
| 6,379,372 B1 | 4/2002 | Dehdashtian et al. | 606/192 |
| 6,387,120 B2 | 5/2002 | Wilson et al. | 623/1.11 |

| | | | | | |
|---|---|---|---|---|---|
| 6,391,050 B1 | 5/2002 | Broome .................. 623/1.11 | 2003/0033001 A1 | 2/2003 | Igaki |
| 6,391,051 B2 | 5/2002 | Sullivan, III et al. | 2003/0055483 A1* | 3/2003 | Gumm .................. 623/1.11 |
| 6,406,487 B2 | 6/2002 | Brenneman .............. 623/1.11 | 2003/0055484 A1 | 3/2003 | Lau et al. .................. 623/1.13 |
| 6,406,489 B1 | 6/2002 | Richter et al. ............. 623/1.16 | 2003/0195546 A1 | 10/2003 | Solar et al. .................. 606/192 |
| 6,416,529 B1 | 7/2002 | Holman et al. ............. 606/194 | 2003/0236531 A1 | 12/2003 | Couvillon, Jr. |
| 6,432,064 B1* | 8/2002 | Hibner et al. .............. 600/564 | 2004/0068161 A1 | 4/2004 | Couvillon, Jr. |
| 6,436,104 B2 | 8/2002 | Hojeibane ................. 606/108 | 2005/0149161 A1 | 7/2005 | Eidenschink et al. |
| 6,443,980 B1 | 9/2002 | Wang et al. ............... 623/1.35 | 2005/0149176 A1 | 7/2005 | Heggestuen et al. |
| 6,468,203 B2 | 10/2002 | Belson | 2005/0154442 A1 | 7/2005 | Eidenschink et al. |
| 6,471,672 B1 | 10/2002 | Brown et al. | 2005/0165439 A1 | 7/2005 | Weber et al. |
| 6,475,166 B1 | 11/2002 | Escano .................. 600/585 | 2005/0182473 A1 | 8/2005 | Eidenschink et al. |
| 6,475,639 B2 | 11/2002 | Shahinpoor et al. | 2005/0187603 A1 | 8/2005 | Eidenschink et al. |
| 6,482,211 B1 | 11/2002 | Choi ..................... 606/108 | 2005/0273149 A1 | 12/2005 | Tran et al. |
| 6,488,694 B1 | 12/2002 | Lau et al. .................. 606/194 | 2006/0206188 A1 | 9/2006 | Weber et al. |
| 6,508,835 B1 | 1/2003 | Shaolian et al. ............ 623/1.35 | 2007/0088256 A1 | 4/2007 | Intoccia |
| 6,514,237 B1* | 2/2003 | Maseda .................. 604/533 | | | |
| 6,514,281 B1 | 2/2003 | Blaeser et al. ............. 623/1.12 | | | |
| 6,520,983 B1 | 2/2003 | Colgan et al. ............. 623/1.11 | | | |

FOREIGN PATENT DOCUMENTS

| | | |
|---|---|---|
| ES | 2048086 | 3/1994 |
| ES | 2062930 | 12/1994 |
| FR | 2 678 508 A1 | 1/1993 |
| GB | 2227020 | 7/1990 |
| JP | 8066351 | 3/1996 |
| JP | 8322783 | 12/1996 |
| JP | 10014863 | 1/1998 |
| WO | WO 01/58973 | 8/2001 |
| WO | 03/017872 A1 | 3/2003 |
| WO | 03/055414 A1 | 7/2003 |
| WO | WO 03/094800 | 11/2003 |
| WO | WO 2004/000141 | 12/2003 |
| WO | WO 2005/025458 | 3/2005 |

| | | |
|---|---|---|
| 6,520,988 B1 | 2/2003 | Colombo et al. ........... 623/1.35 |
| 6,530,947 B1 | 3/2003 | Euteneuer et al. .......... 623/1.11 |
| 6,533,805 B1 | 3/2003 | Jervis .................. 623/1.11 |
| 6,540,719 B2 | 4/2003 | Bigus et al. .............. 604/96.01 |
| 6,545,097 B2 | 4/2003 | Pinchuk et al. |
| 6,554,841 B1 | 4/2003 | Yang .................. 606/108 |
| 6,582,459 B1 | 6/2003 | Lau et al. .................. 623/1.11 |
| 6,583,533 B2 | 6/2003 | Pelrine et al. |
| 6,586,859 B2 | 7/2003 | Kornbluh et al. |
| 6,589,251 B2 | 7/2003 | Yee et al. |
| 6,589,262 B1 | 7/2003 | Honebrink et al. .......... 606/191 |
| 6,592,616 B1 | 7/2003 | Stack et al. |
| 6,596,020 B2 | 7/2003 | Vardi et al. |
| 6,599,315 B2 | 7/2003 | Wilson .................. 623/1.11 |
| 6,602,226 B1 | 8/2003 | Smith et al. ............ 604/103.05 |
| 6,607,506 B2 | 8/2003 | Kletschka ................ 604/96.01 |
| 6,613,067 B1 | 9/2003 | Johnson .................. 606/194 |
| 6,629,981 B2 | 10/2003 | Bui et al. .................. 606/108 |
| 6,664,718 B2 | 12/2003 | Pedrine et al. |
| 6,669,718 B2 | 12/2003 | Besselink |
| 6,679,836 B2 | 1/2004 | Couvillon, Jr. |
| 6,733,520 B2 | 5/2004 | Yang et al. |
| 6,749,556 B2 | 6/2004 | Banik |
| 6,752,433 B2 | 6/2004 | Frost |
| 6,764,504 B2 | 7/2004 | Wang et al. |
| 6,770,027 B2 | 8/2004 | Banik et al. |
| 6,783,542 B2 | 8/2004 | Eidenschink |
| 6,802,856 B2 | 10/2004 | Wilson |
| 6,835,173 B2 | 12/2004 | Couvillon, Jr. |
| 6,849,085 B2 | 2/2005 | Marton |
| 6,884,258 B2 | 4/2005 | Vardi et al. |
| 6,969,395 B2 | 11/2005 | Eskuri |
| 7,018,402 B2 | 3/2006 | Vito et al. |
| 7,063,671 B2 | 6/2006 | Couvillon, Jr. |
| 7,070,613 B2 | 7/2006 | Weber et al. |
| 7,225,518 B2 | 6/2007 | Eidenschink et al. |
| 7,314,480 B2 | 1/2008 | Eidenschink et al. |
| 7,331,969 B1 | 2/2008 | Inganas et al. |
| 7,338,509 B2 | 3/2008 | Mattison |
| 7,367,989 B2 | 5/2008 | Eidenschink |
| 7,379,852 B2 | 5/2008 | Freitas et al. |
| 7,396,582 B2 | 7/2008 | Claude et al. |
| 7,399,311 B2 | 7/2008 | Bertolino et al. |
| 2001/0032013 A1* | 10/2001 | Marton .................. 623/1.15 |
| 2001/0049548 A1 | 12/2001 | Vardi et al. ............... 623/1.11 |
| 2002/0019664 A1 | 2/2002 | Douglas .................. 623/1.35 |
| 2002/0019665 A1 | 2/2002 | Dehdashtian et al. ...... 623/1.35 |
| 2002/0022874 A1 | 2/2002 | Wilson .................. 623/1.11 |
| 2002/0038140 A1 | 3/2002 | Yang et al. ............... 623/1.12 |
| 2002/0038141 A1 | 3/2002 | Yang et al. ............... 623/1.12 |
| 2002/0072755 A1 | 6/2002 | Bigus et al. .................. 606/108 |
| 2002/0107330 A1* | 8/2002 | Pinchuk et al. ............. 525/242 |
| 2002/0111675 A1 | 8/2002 | Wilson .................. 623/1.35 |
| 2002/0116045 A1 | 8/2002 | Eidenschink .............. 623/1.11 |
| 2002/0120320 A1 | 8/2002 | Wang et al. ............... 623/1.11 |

OTHER PUBLICATIONS

U.S. Appl. No. 10/747,546, filed Dec. 29, 2003, Eidenschink et al.
Foley et al., "Bifurcation Lesion Stenting", *The Thoraxcentre Journal*, vol. 8, No. 4, (1996).
Schampaert, MD, Erick et al., "The V-Stent: A Novel Technique for Coronary Bifurcation Stenting", *Catheterization and Cardiovascular Diagnosis*, 39:320-326 (1996).
Pomerantz, MD, et al., "Distortion of Palmaz-Schatz Stent Geometry Following Side-Branch Balloon Dilation Through the Stent in a Rabbit Model", *Catheterization and Cardiovascular Diagnosis*, 40:422-426 (1997).
Palmaz, MD, et al., "Aortic Bifurcation Stenosis: Treatment with Intravascular Stents", *Journal of Vascular and Interventional Radiology*, vol. 2, No. 3, pp. 319-323 (Aug. 1991).
Oda, MD., et al., "Fork Stenting for Bifurcational Lesion", Journal of Interventional Cardiology, vol. 9, No. 6, pp. 445-454 (Dec. 1996).
Nakamura et al., "Techniques for Palmaz-Schatz Stent Deployment in Lesions With a Large Side Branch", Catheterization and Cardiovascular Diagnosis, vol. 34, pp. 353-361 (1995).
Bar-Cohen et al., "Electro-Active Polymer (EAP) Actuators for Planetary Applications," Proceedings of SPIE Annual International Symposium on Smart Structures and Materials, 5 pages, 1999.
Bar-Cohen, "Application of Dielectric Elastomer EAP Actuators," Electroactive Polymer (EAP) Actuators as Artificial Muscles, Chapter 16, pp. 457-495, 2001.
Bar-Cohen, "EAP Applications, Potential, and Challenges," Electroactive Polymer (EAP) Actuators as Artificial Muscles, Chapter 21, pp. 615-659, 2001.
Bar-Cohen, "EAP History, Current Status, and Infrastructure," Electroactive Polymer Actuators (EAP) as Artificial Muscles, Chapter 1, pp. 3-43, 2001.
Bar-Cohen, "Electroactive Polymers as Artificial Muscles-Capabilities, Potentials and Challenges," Handbook on Biommetics, Section 11, Chapter 8, Aug. 2000.
Bar-Cohen, "Transition of EAP Material from Novelty to Practical Applications—Are we there Yet?," Proceedings of SPIE vol. 4329, pp. 1-6, Mar. 5-8, 2001.
Bar-Cohen, "WorldWide ElectroActive Polymers WW EAP (Artificial Muscles) Newsletter," vol. 3, No. 1, pp. 1-14, Jun. 2001.
Brock, "Review of Artificial Muscle Based on Contractile Polymers," 12 pages, May 9, 2002.

Buckley, "EAP DARPA," Defense Sciences Office, 8 pages, Jan. 2002.

Cho et al., "Development of Micro Inchworm Robot Actuated by Electrostrictive Polymer Actuator," Proceedings of SPIE, vol. 4329, pp. 466-474, Mar. 5-8, 2001.

Goodell, "Laser Thromolysis (LT) for Stroke," http://www.providence.org/Oregon/Programs_and_Services/Research/Laser_Center/Lt_Stroke..., 3 pages, Updated Mar. 26, 2001, printed Oct. 2, 2002.

Gulch et al., "Characterization of Electroactive Behavior and of Progress in Developments and Applications of Ionic Polymer Gels," Proceedings of SPIE vol. 4695, pp. 367-377, 2002.

http://ais.gmd.de/BAR/snake.html, "GMD-SNAKE, Robot-Snake with Flexible Real-Time Control," 3 pages, last updated Jan. 10, 2001, printed Dec. 27, 2001.

http://nanobio.snu.ac.kr/eng/research_5.html, "Electroactive Polymer," Nano Bioelectronics & Systems Research Center, 1 page, printed Feb. 5, 2004.

http://omlc.ogi.edu/projects/lt/, "Laser Thrombolysis," 9 pages, Dec. 12, 1996.

http://piaggio.ccii.unipi.it/cathe.htm, "Smart Catheters," 1 page, printed Aug. 27, 2001.

http://polysep.ucla.edu/Research20%Advances, "Polymers and Separations Research Lab (PolySep)," 12 pages, printed Feb. 5, 2004.

http://robby.caltech.edu/~chen/res-medical.html, "Snake-Like Robot Endoscopes," 2 pages, updated Aug. 14, 1996, printed Dec. 27, 2001.

http://virtualskies.arc.nasa.gov./research/youDecide, "Eletroactive Polymers 2: Ionic and Conductive Polymers," 2 pages, printed Feb. 5, 2004.

http://www.agip.sicences.univ-metz.fr/mihalach/Coperinicus_projet_engl.html, "Snake-Like Flexible Micro-Robot," 6 pages, printed Dec. 27, 2001.

http://www.azom.com/detailsasp?ArticleID=885, "Electroactive Polymers— EAPs, 7 pages, Feb. 5, 2004.

http://www.designinsite.dk/htmsider/m1328.htminsider, 3 pages, printed Mar. 11, 2004.

http://www.erg.sri.com/automation/actuators.html, "Artificial Muscle Transducers," 3 pages, printed Feb. 5, 2004.

http://www.nasatech.com/Briefs/Oct01/NPO20613.html, "Miniature Electroactive-Polymer Rakes," 2 pages, Feb. 5, 2004.

Ikuta et al., "Shape Memory Alloy Servo Actuator System with Electric Resistance Feedback and Application for Active Endoscope," IEEE Internation Conference on Robotics and Automation, pp. 427-430, Apr. 24-29, 1988.

Immerstrand et al., "Conjugated-Polymer Micro-and Milliactuators for Biological Applications," MRS Bulletin, pp. 461-464, Jun. 2002.

Jager et al., "Applications of Polypyrrole Microactuators," SPIE, vol. 3669, pp. 377-384, Mar. 1999.

Jager et al., "Microfabricating Conjugated Polymer Actuators," Science, vol. 290, pp. 1540-1545, Nov. 24, 2000.

Kubler et al., "An Endoscopic Navigation System," Medicine Meets Virtual Reality, pp. 253, 255, 2001.

Kubler et al., "Endoscopic Robots," Proceedings of the $3^{rd}$ International Conference on Medical Image Computing and Computer-Assisted Intervention—MICCAI, pp. 949-955, 2000.

Madden et al., "Conducting Polymer Actuators as Engineering Materials," Proceedings of SPIE vol. 4695, 2002.

Madden et al., "Polypyrrole Actuators: Modeling and Performance," Proceedings of SPIE vol. 4329, pp. 72-83, Mar. 5-8, 2001.

Madden, "Conducting Polymer Actuators," Abstract, 2 pages, Sep. 2000.

Mazzoldi et al., "Conductive Polymer Based Structures for a Steerable Catheter," Proceedings of SPIE vol. 3987, pp. 273-280, 2000.

Nam, "Electroactive Polymer (EAP) Actuators and Devices for Micro-Robot Systems," 1 page, Nov. 28, 2000.

Otero et al., "EAP as Multifunctional and Biommetic Materials," SPIE, vol. 3669, pp. 26-34, Mar. 1999.

Peirs et al., "Miniature Parallel Manipulators for Integration in a Self-Propelling Endoscope," 1 page, IMechs Workshop, Oct. 27, 1999.

Pelrine et al., "Applications of Dielectric Elastomer Actuators," Proceedings of SPIE vol. 4329, pp. 335-349, Mar. 5-8, 2001.

Rocchia et al., "Exploiting Conducting Polymer Fiber Radial Expansion for Bioinspired Actuation," Proceedings of SPIE vol. 5051, pp. 453-457, 2003.

Sahoo et al., "Actuators Based on Electroactive Polymers," Current Science, vol. 81, No. 7, pp. 743-746, Oct. 10, 2001.

Sansinena et al., "Chapter 7, Conductive Polymers," Electroactive Polymer Actuators (EAP) as Artificial Muscles, Edited by Bar-Cohen, pp. 193-221, 2001.

Santa et al., "Intravascular Microcatheters Steered by Conducting Polymer Actuators," $18^{th}$ International Conference of the IEEE Engineering in Medicine and Biology Society, pp. 2203-2204, 1996.

Smela et al., "Electrochemically Driven Polypyrrole Bilayers for Moving and Positioning Bulk Micromachined Silicon Plates," Journal of Microelectromechanical Systems, vol. 8, No. 4, pp. 373-383, Dec. 1999.

Smela et al., "Thiol-Modified Pyrrole Monomers: 1. Synthesis, Characterization, and Polymerization of 1-(2-Thioethyl) Pyrrole and 3-(2-Thioethyl) Pyrrole," Langmuir, vol. 14, 2970-2975, May 26, 1998.

Smela, "Conjugated Polymer Actuators for Biomedical Applications," Advanced Materials, vol. 15, No. 6, pp. 481-494, Mar. 17, 2003.

Smela, "Microfabrication of PPy Microactuators and Other Conjugated Polymer Devices," Journal of Micromechanics and Microengineering, vol. 9, pp. 1-18, 1999.

Wax et al., "Compliant Actuators Based on Electroactive Polymers," Materials Research Society Proceedings, vol. 600, pp. 3-11, 2000.

Zhou et al., "Actuators for the Cochlear Implant," Synthetic Metals, vol. 135-136, pp. 39-40, 2003.

* cited by examiner

ROTATABLE CATHETER ASSEMBLY

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Description of the Related Art

Stent delivery systems for deployment of one or more stent bodies at or around a vessel bifurcation have been proposed. Often such stents generally have an opening which allows for unimpeded blood flow into one or more side branch arteries, and/or through which an additional stent body may be deployed. However, problems are still encountered in orienting a stent relative to the side branch at the bifurcation of the primary and secondary passages. Moreover, such bifurcated assemblies are typically specially manufactured at an increased cost over a more standard stent intended for single vessel deployment.

In delivering a stent to a vessel location, many current devices rely on either passive torque (e.g., pushing the stent forward and allowing the stent that is fixed on the guidewire/balloon to passively rotate itself into place) or creating torque from outside of the patient to properly orient the medical device in the passage. Such catheter assemblies include those described in U.S. Pat. No. 5,749,825; U.S. Pat. No. 6,599,315 and U.S. Pat. No. 6,290,673 the entire content of each of which being incorporated herein by reference.

Unfortunately such devices still often require a significant portion of the catheter assembly in addition to the balloon to be subjected to torque in order to align the stent with the side branch opening of the bifurcation. Subjecting the catheter as well as a vessel to such extraneous torque may be considered undesirable.

Thus, a need exists to provide a catheter which is capable of allowing a medical device such as a stent to be easily maneuvered and aligned at a vessel bifurcation or other location without the need to torque or rotate the entire catheter shaft in order to align the stent at a vessel bifurcation. Various devices and methods described herein address this need by providing a catheter system with a rotatable balloon about which a stent may be mounted on or engaged to. The rotatable balloon is independently rotatable relative to the inner and/or outer catheter shafts thereby eliminating the need to apply torque to the catheter shaft to align the stent at a vessel bifurcation.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

As used herein the term 'stent' refers to an expandable prosthesis for implantation into a body lumen or vessel and includes devices such as stents, grafts, stent-grafts, vena cava filters, etc. In some embodiments a stent may be at least partially constructed of any of a variety of materials such as stainless steel, nickel, titanium, nitinol, platinum, gold, chrome, cobalt, as well as any other metals and their combinations or alloys. A stent may be at least partially constructed of a polymer material. A stent may be at least partially constructed of a shape-memory polymer or material. A stent may be balloon expandable, self-expandable, hybrid expandable or a combination thereof. In some embodiments a stent may include one or more areas, bands, coatings, members etc that is (are) detectable by imaging modalities such as X-Ray, MRI or ultrasound. In some embodiments at least a portion of the stent is at least partially radiopaque. In some embodiments a stent may include one or more therapeutic and/or lubricious coatings applied thereto.

Some embodiments of the present invention are directed to catheter systems wherein the catheter comprises balloon which is independently rotatable about the catheter shaft or shafts. For example, in at least one embodiment the invention is directed to a catheter having an inner shaft wherein a distal waist of the balloon is rotatably engaged and an outer shaft wherein a proximal waist of the balloon is rotatably engaged. In some embodiments the catheter comprises only a single catheter shaft about which the balloon is rotatably engaged.

In at least one embodiment each balloon waist is disposed about a collar, the collar may be fixedly engaged to a portion of the catheter shaft or may be selectively rotatable there about. In at least one embodiment a first portion of a catheter shaft has a collar engaged there to, the collar may be fixed or rotatable thereabout. Where the collar is fixed a rotatable balloon is disposed about the catheter shaft in a manner such that each waist of the rotatable balloon is rotatably disposed about a collar. Where the collars are rotatable about the catheter shaft, each waist of the balloon is fixedly disposed to the outer surface of a collar so that the balloon is made rotatable about the catheter shaft as a result.

The collars are at least partially constructed of an electro-active polymer (EAP) which expands to a predetermined extent upon exposure to an electric current. In some embodiments the collars are exposed to the electric current by a conductive element. A second conductive element is provided by exposing the fluid that inflates the balloon, which is typically saline and/or a radiopaque solution) to a similar electrical current. In some embodiments the EAP material of the collar and/or the collar itself will expand about 0.5% to about 20% expansion in a predetermined manner and/or direction when subjected to an electric current of 0.001 microAmps to 1 milliAmps (−2 to +2 V). In at least one embodiment a collar is constructed of one or more conductive elements such as gold, silver, platinum, etc., which is at least partially surrounded by a layer of EAP material.

In embodiments where the collars are rotatable about the catheter shaft, prior to exposure to the electric current the collars define an inside diameter which is sufficiently greater than the outer diameter of the catheter shaft to which they are respectively engaged so as to allow the collars, and thus the balloon mounted thereto, to freely rotate about the catheter shaft(s). When the collars are exposed to the electric current through one or more conductive members within and/or adjacent to the catheter the collars will expand and thus effectively contract around the respective catheter shaft to which they are engaged, effectively sealing the interior of the balloon which may then be expanded.

In embodiments where the collars are fixed to the catheter shaft, prior to exposure to the electric current the collars define an outside diameter which is sufficiently less than the inner diameter of the catheter waists which are respectively disposed there about so as to allow the waists, and thus the balloon body extending there between, to freely rotate about the collars. When the collars are exposed to the electric current through one or more conductive members within and/or adjacent to the catheter the collars will expand and thus effectively push against the respective catheter waists, effectively sealing the interior of the balloon which may then be expanded.

In order to get an electric current to a collar, in some embodiments a conductive wire or member of gold, gold plated SS, Nitinol, silver coated SS, Elgiloy, etc. extends from a current source to a collar through or adjacent to the catheter shaft. In some embodiments the conductive member is in the form of an insulated wire or other member which engages the collar via an exposed end which extends through an opening in the catheter shaft. Such a member may be co-extruded with one or more catheter shafts and/or balloon. A proximal end of the wire is engaged to a current source which may be activated to transmit the current through the wire to the collar when desired. In at least one embodiment a conductive member is at least partially contained within one or more lumens defined by the catheter.

In some embodiments a collar is bonded, welded, adhesively engaged, mechanically engaged or otherwise fixed to a balloon waist. In some embodiments a collar is bonded, welded, adhesively engaged, mechanically engaged or otherwise engaged to a portion of the catheters shaft underlying a waist of the balloon which is rotatable thereabout. In some embodiments, where the collar is fixed to a balloon waist the waist may be reinforced with one or more layers of transition material positioned between the collar and the balloon waist in order to facilitate engagement there between. In some embodiments the waist may likewise be reinforced. In some embodiments a transition material includes but is not limited to: Plexar, Selar, EMS Hytrel, and other similar materials. In at least one embodiment the collar is integral with the balloon waist. In at least one embodiment the collar is integral with the catheter shaft. In at least one embodiment a collar comprises only EAP material.

In some embodiments the catheter comprises one or more support members or rings which support the region of the catheter shaft(s) about which the collars are mounted. A support ring may be constructed of one or more materials including but not limited to: Polyamide, Nylon, Pebax, Acetyl, PTFE, HDPE, PI, PET, Christamid, Vestimid, metal reinforced polymers, braided reinforced polymers, Stainless steel, Nitinol, etc.

In some embodiments the catheter is disposed about a primary guidewire. In at least one embodiment the catheter is a fixed wire catheter. In some embodiments a secondary guidewire housing through which a side branch or secondary guidewire is positioned. In some embodiments the secondary guidewire housing is engaged to the balloon. In at least one embodiment the secondary guidewire housing is positioned at least partially under the stent prior to delivery.

In some embodiments the secondary guidewire extends into a side branch of a bifurcation through a secondary opening of the stent. By advancing the catheter along the secondary guidewire as the catheter is advanced through the main vessel to the bifurcation rotation will be imparted to the balloon to orient the secondary opening of the stent and/or the secondary guidewire housing with the side branch of the vessel bifurcation. When properly oriented the collars are subjected to an electric current thereby imparting the balloon with a fluid seal sufficient to allow inflation of the balloon.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
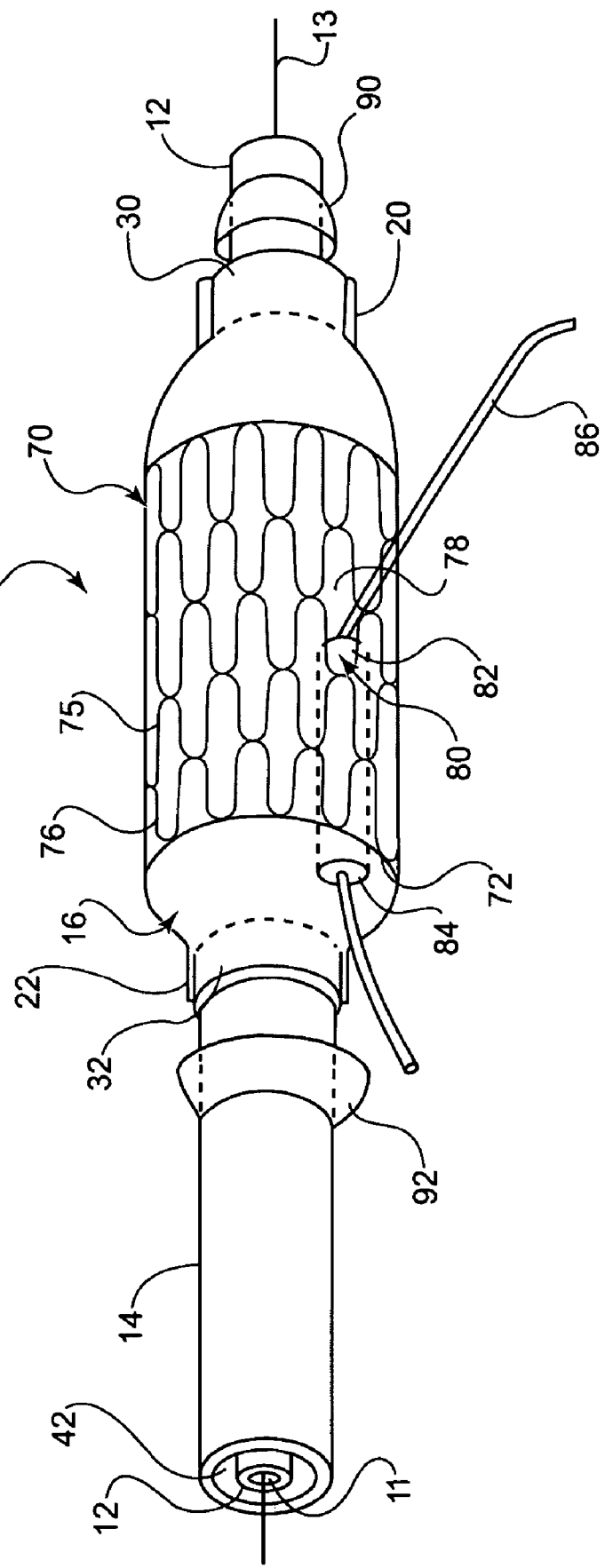
FIG. 1 is a perspective view of an embodiment of the invention comprising a catheter assembly having a rotatable balloon.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring now to the drawings which are for the purposes of illustrating embodiments of the invention only and not for purposes of limiting same, in at least one embodiment of the invention, an example of which is shown in FIG. 1, a catheter assembly 10 comprises an inner catheter shaft 12, an outer catheter shaft 14 and a rotatable balloon 16 rotatably engaged to one or both shafts 12 and 14.

Balloon 16 may be a typical angioplasty, stent delivery balloon or other inflatable member which may be used or incorporated into a catheter assembly. Typically the wall thickness of the waists 20 and 22 of the balloon 16 will be thicker than the thickness of the balloon body which extends there between. In some cases the thickness of one or both waists is about twice that of the balloon body but may be about 10 times more resistant to radial pressures.

In order to allow the balloon 16 to rotate freely relative to the shaft or shafts 12 and 14 each waist 20 and 22 of the balloon 16 is engaged to a collar 30 and 32 respectively. Collars 30 and 32 are at least partially constructed of EAP material such including of Poly-pyrrole (PPY), Poly-Aniline (PAni), Poly-Thiofene (PTH), Poly-Paraphenylene Vinylene (PPV), Nafion, Bucky paper or any other ionic electro-active polymer that is considered to have low voltage, low speed, high stress (up to 500 MPa), characteristics. EAP materials have the unique characteristic of expanding in size when exposed to an electric current of predetermined current or voltage. For example, in some embodiments the EAP material of the collar and/or the collar itself will expand about 0.5% to about 20% when exposed to an electric current of 0.001 microAmps to 1 milliAmps (−2 to +2 V).

EAP materials and some of their notable characteristics are described in an article entitled *Electro-Active Polymer Actuators for Planetary Applications* by Y. Bar-Cohen et al. and published in Paper No. 3669-05 of the Proceedings of SPIE Annual International Symposium on Smart Structures and Materials, March 1999, Newport Beach, Calif. SPIE Copyright 1999, the entire contents of which being incorporated herein by reference.

As a result of EAP materials unique expansion characteristics a collar comprising EAP material such as collars 30 and 32 may be formed to have a pre-current shape and a post-current shape that is different or larger than the pre-current shape.

Pre-current refers to the condition of the collars 30 and 32 before the collars are exposed to an electric current sufficient to activate the EAP material. Post-current refers to the condition of the collars 30 and 32 when the collars are being exposed to an electric current sufficient to activate the expansion of the EAP material.

Figure 2:
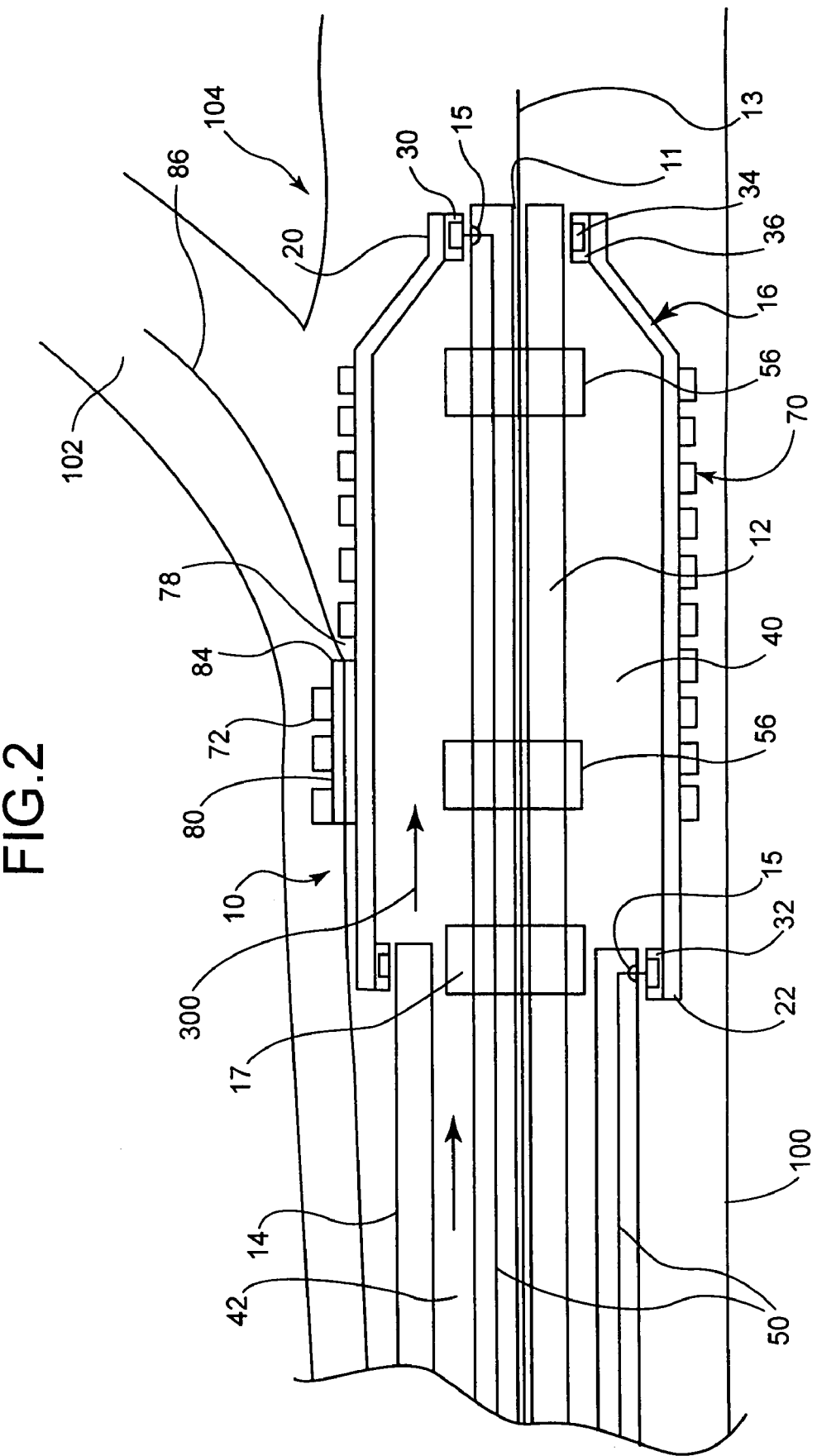
FIG. 2 is a longitudinal cross-sectional view of an embodiment of the invention being advanced to a vessel bifurcation and prior to balloon expansion.

In some embodiments the collars 30 and 32 in the pre-current state, are constructed to rotate freely about the respective catheter shafts 12 and 14 and to become fixed in position and engagement to the respective catheter shafts 12 and 14 in the post current state. In such embodiments, an example of which is shown in FIGS. 2 collars 30 and 32 are provided with a pre-current inner diameter, which is sufficiently greater than the outer diameter of the shafts 12 and 14 to allow the collar, and thus the balloon 16 engaged thereto, to freely rotate about the shafts 12 and 14 before exposure to the electric current.

Figure 3:
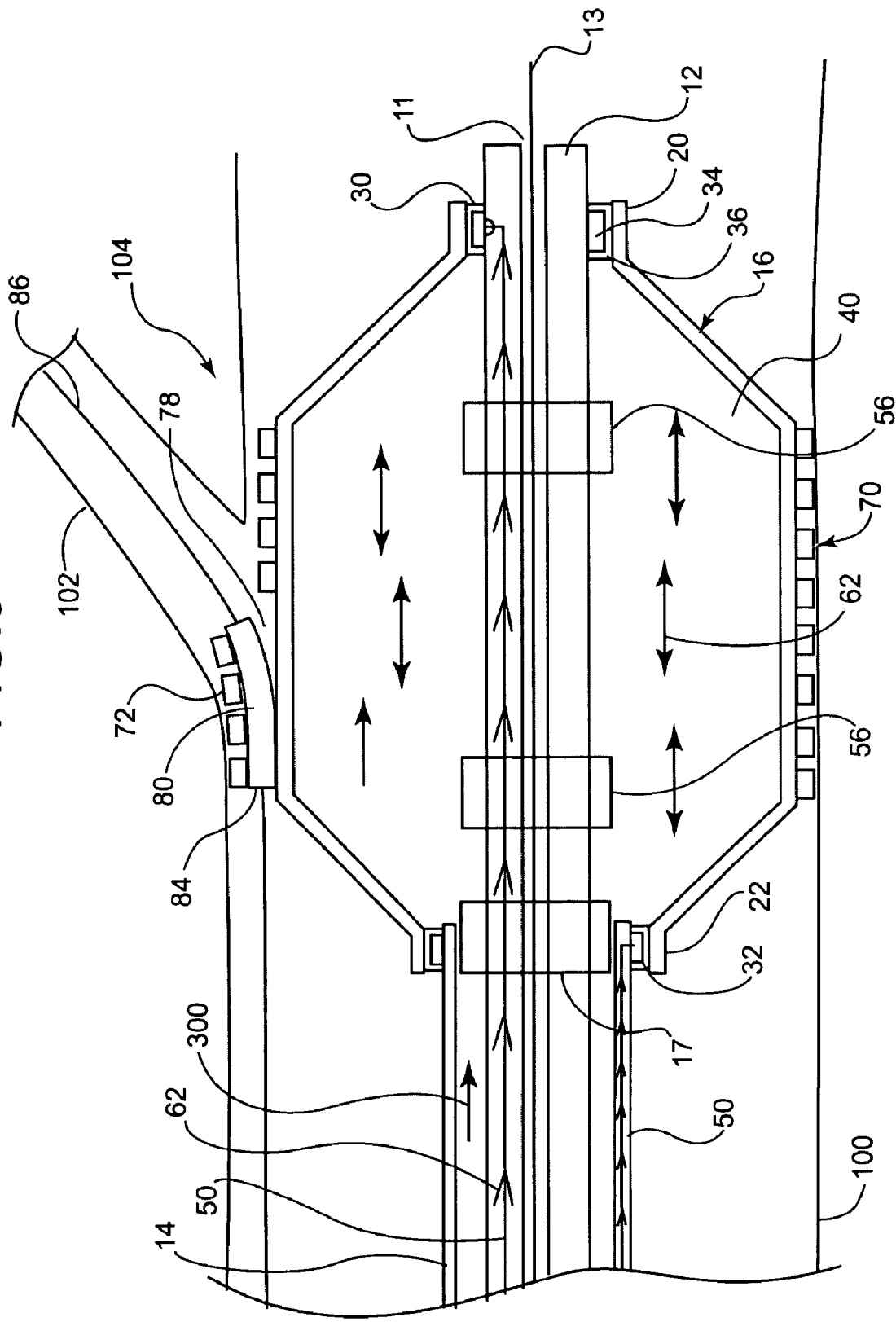
FIG. 3 is a longitudinal cross-sectional view of the embodiment shown in FIG. 2 shown during expansion of the balloon.

When the collars 30 and 32 are exposed to an electric current, illustrated by arrows 62, the expansion of the EAP material causes the inner diameter of the collars to expand such as is shown in FIG. 3. As a result, each collar 30 and 32 will contract around their respective catheter shafts 12 and 14 effectively sealing the collars 30 and 32 thereto. As a consequence of the collars 30 and 32 being sealed against the shafts 12 and 14, the interior 40 of the balloon 16 is made effectively fluid tight against the shafts thereby allowing the balloon to be expanded such as by inflation via an inflation fluid through inflation lumen 42.

Figure 4:
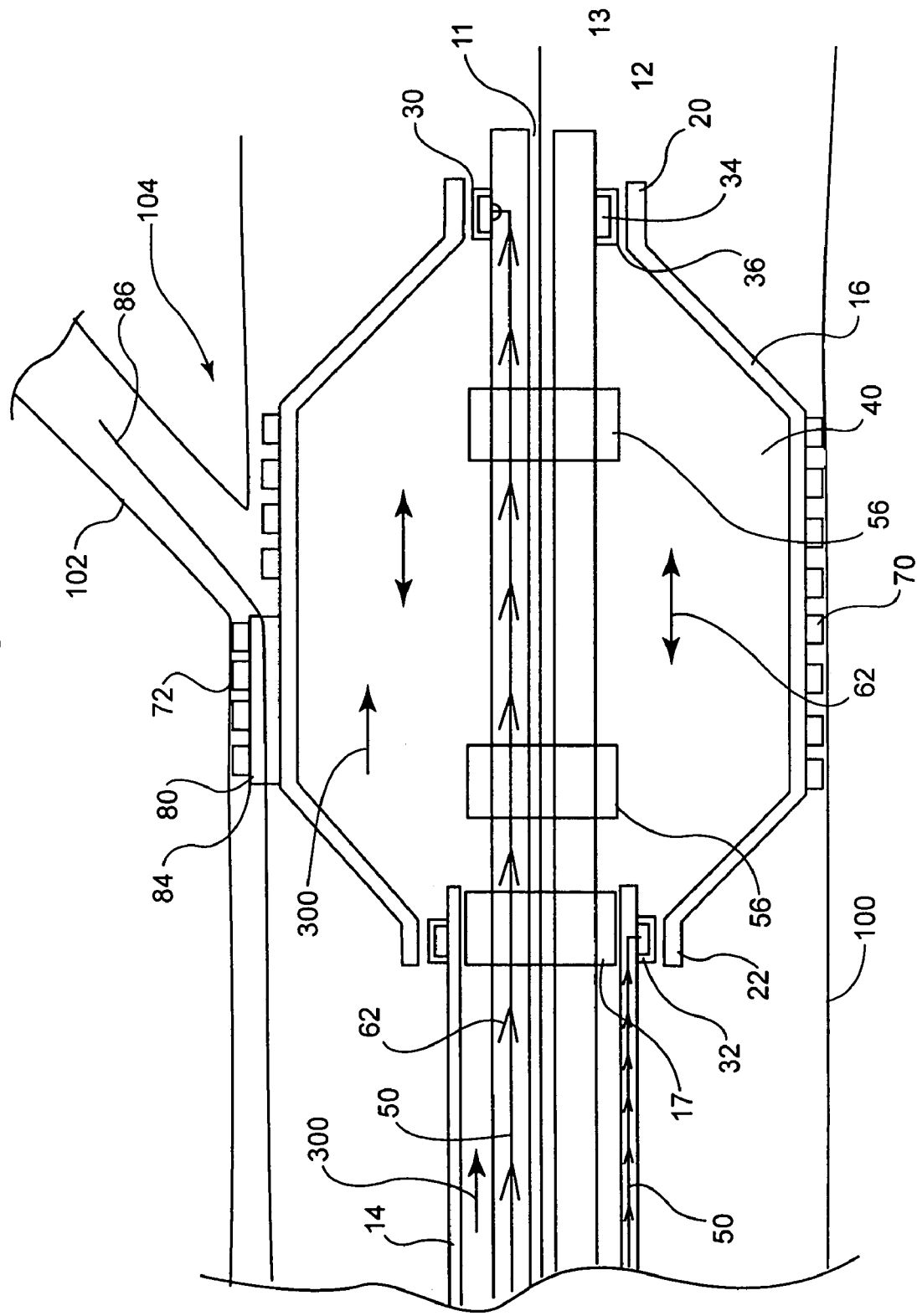
FIG. 4 is a longitudinal cross-sectional view of an embodiment of the invention being advanced to a vessel bifurcation and prior to balloon expansion.
Figure 5:
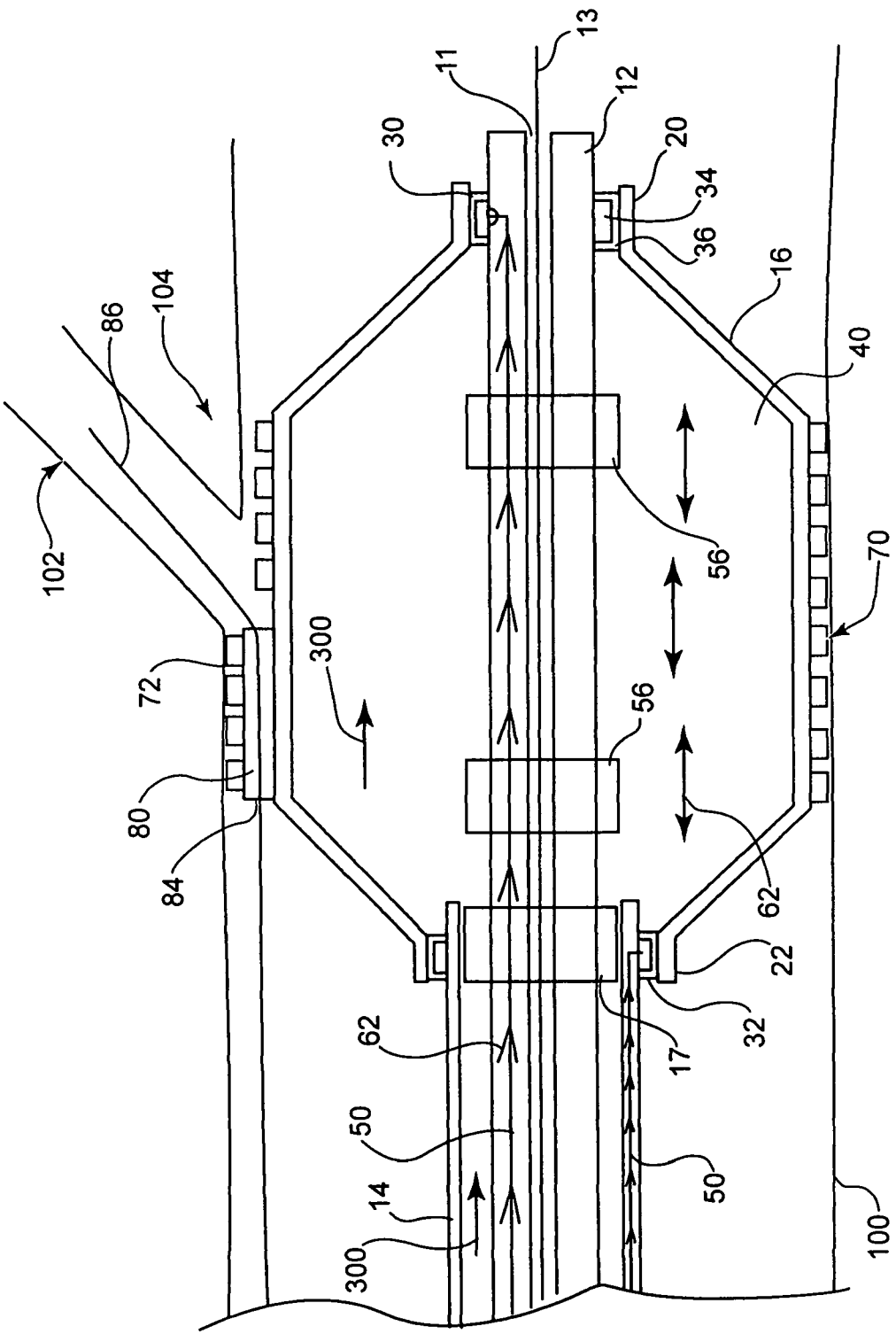
FIG. 5 is a longitudinal cross-sectional view of the embodiment shown in FIG. 4 shown during expansion of the balloon.

In some embodiments, an example of which is shown in FIG. 4, the collars 30 and 32 are fixedly engaged about shafts 12 and 14 respectively. In the pre-current state, the balloon 16 is rotatably disposed about the collars 30 and 32 such that the distal waist 20 of the balloon 16 is rotatably disposed about the distal collar 30 and the proximal waist 22 of the balloon 16 is rotatably disposed about the proximal collar 32 of the balloon 16. In the pre-current state each collar 30 and 32 has an outer diameter less than the inner diameter defined by the respective balloon waists 20 and 22. In the post-current state the collars 30 and 32 expand outward to engaged the waists 20 and 22 such as in the manner shown in FIG. 5. By engaging the waists 20 and 22 in this manner the interior 40 of the balloon 16 is made effectively fluid tight against the collars 30 and 32 thereby allowing the balloon to be expanded such as by inflation via an inflation fluid through inflation lumen 42.

In some embodiments, such as in the example shown in FIGS. 2-5, it may be beneficial to support the distal end of the outer shaft 14 with a support ring or member 17. The support ring may be disposed about the inner shaft 12 and/or may be merely internally engaged to the outer shaft 14. In some embodiments the ring 17 extends between the inner shaft 12 and the outer shaft 14 but defines one or more openings there through which further define the inflation lumen 42. Ring 17 may be constructed of one or more materials including but not limited to: stainless steel coil, stainless steel stent like structure, stainless steel spiral cut hypotube, Nitinol, acetyl, PI, HDPE, LX2/TR55, Nanocomposites, Ceramics. In some embodiments the length of the ring 17 will be approximately the same length as the collar 32 and/or 30 which it supports.

In some embodiments the inner shaft 12 has one or more bands 56 of radiopaque material. In some embodiments a band(s) 56 is detectable by imaging modalities such as X-Ray, MRI or ultrasound.

Figure 6:
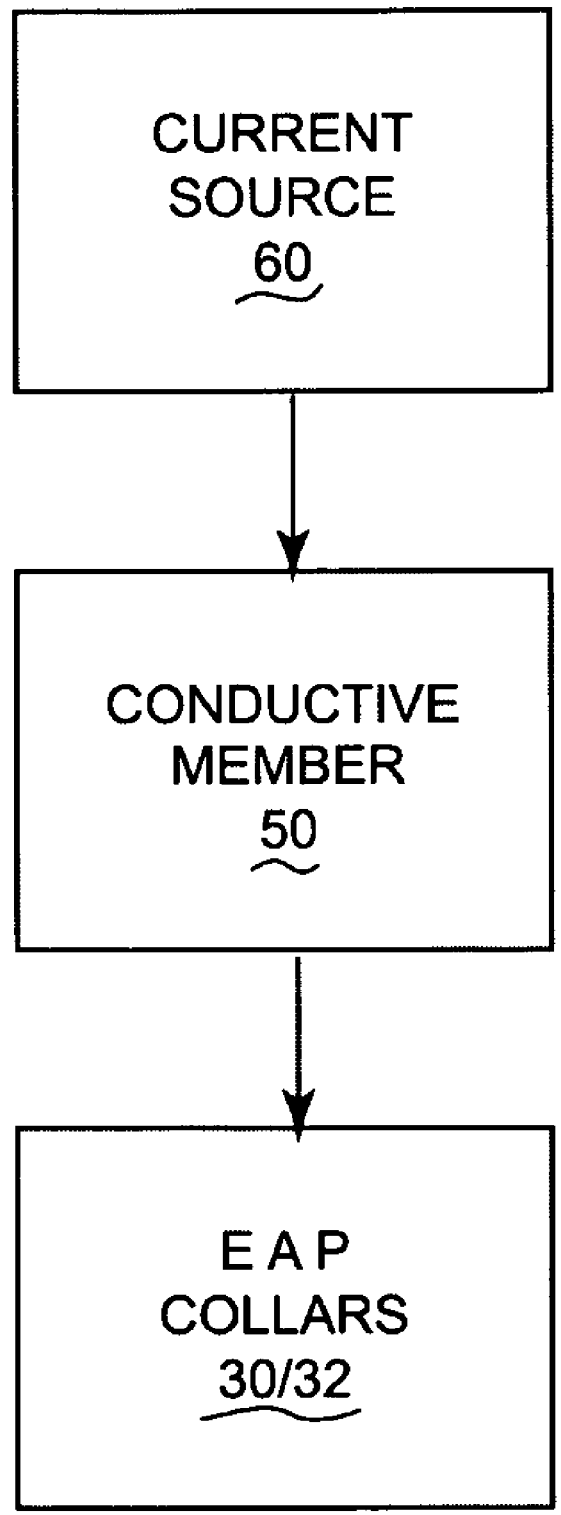
FIG. 6 is a block diagram illustrating the conductive relationship of the catheter assembly shown in FIG. 1 with a source of electric current.

As shown in FIGS. 2-5, one or more conductive wires or other members 50 may extend from a proximal region of the catheter 10 to the collars 30 and 32. A current source 60 as depicted in FIG. 6 is in communication with the wire(s) 50 which when activated transmits the electric current, illustrated by arrows 62 in FIG. 2-5, to the wires 50 and collars 30 and 32, thereby causing expansion of the EAP material in the collars to sealingly engage the balloon 16 to the shafts 12 and 14. The circuit which the current traverses through the members 50 and collars 30 and 32 may be completed as a result of the conductive nature of the saline or other fluid 300 which is used to expand the balloon 16. In some cases the conductive nature of some bodily fluids may also be utilized to complete the circuit.

Wires 50 maybe co-extruded with the material of either or both catheter shafts 12 and 14. An opening 15 in the shaft(s)

exposes the wire 50 to the collars 30 and 32 in the manner shown in FIGS. 2-5. Alternatively, the catheter assembly 10 may define any number of lumens through which a wire or wires may be positioned. In some embodiments a wire 50 may extend at least partially through the inflation lumen 42 to one or both collars 30 and 32.

As indicated above the collars 30 and 32 are at least partially constructed of one or more EAP materials. However, in order to more effectively transmit the electric current to the EAP material in some embodiments, such as shown in FIGS. 2-5, the collars 30 and 32 include a conductive member or marker 34 about which at least one layer 36 of EAP material is engaged. The markers 34 may be any type of conductive material or materials and is preferably biocompatible. Appropriate materials for the construction of the markers 34 include but are not limited to, gold, platinum, nitinol, silver, etc. The layer 36 of EAP material may partially or entirely surround the marker 34.

In the embodiment depicted in FIGS. 2-5, the collars 30 and 32 are constructed so that at least a portion of the inside surface of the collar is defined by a marker 34. This allows direct contact of the conductive material of the marker to be directly engaged to the conductive wire 50. In this manner the current received by the marker may be distributed to the surrounding layer of EAP material in a substantially uniform manner to allow the EAP material engaged thereto to expand in a substantially uniform manner.

As illustrated in FIG. 1 the catheter may be equipped with one or more hubs, tips rings or other devices 90 and/or 92 which may abut the collars 30 and/or 32 to limit the potential for undesired longitudinal migration of the balloon 16 relative to the catheter shafts 12 and 14. In the embodiment shown in FIG. 7, the outer shaft 14 is provided with a necked region 91 wherein the outer and/or inner diameter of the shaft 14 narrows adjacent to the proximal collar 32. The reduced diameter necked region 91 may include a step or shoulder 93 which may abut the proximal collar 32 and/or proximal waist 22 thereby preventing longitudinal migration of the balloon 16 in the proximal direction.

Figure 7:
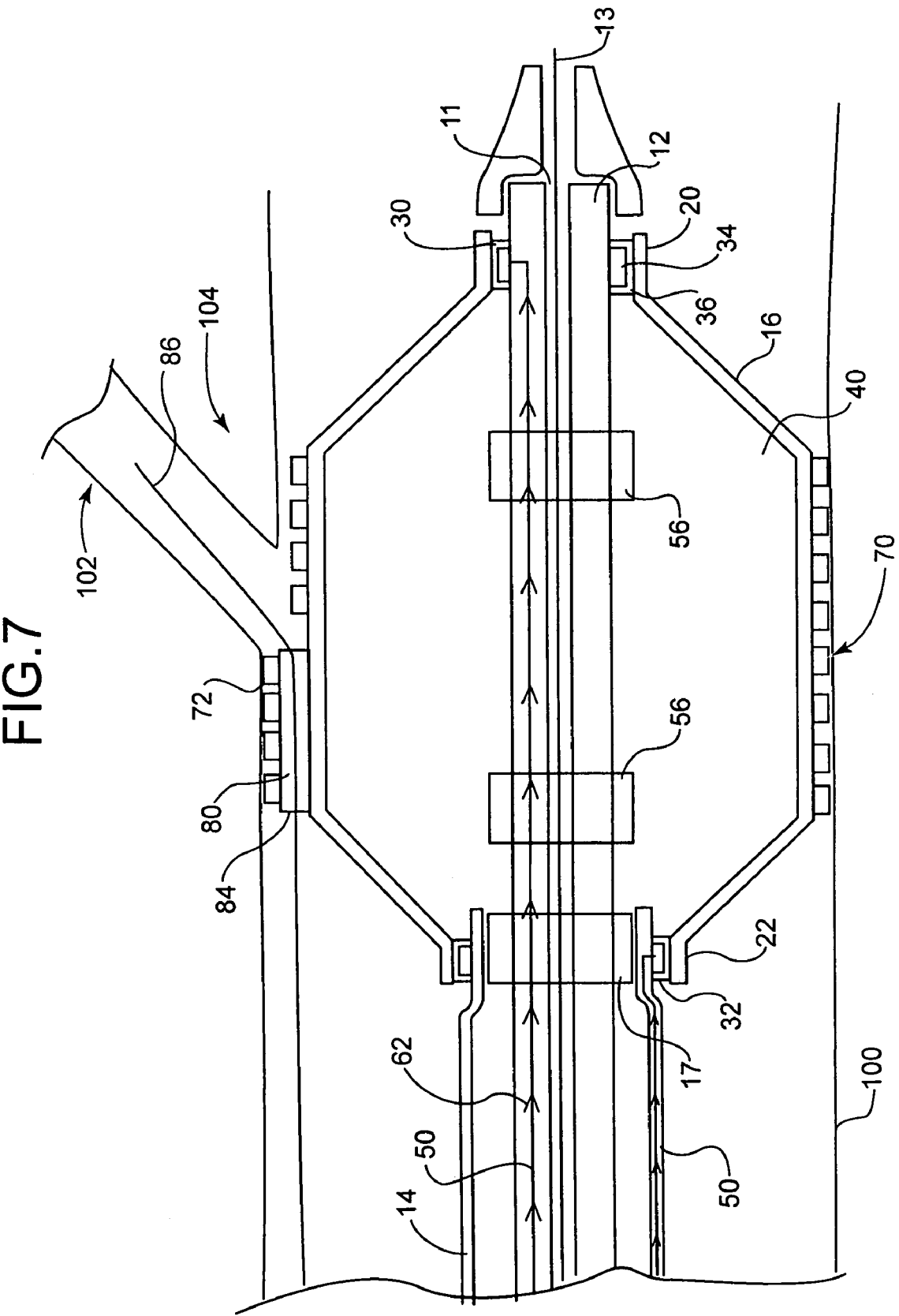
FIG. 7 is a longitudinal cross-sectional view of an embodiment of the invention.

As is also shown in FIG. 7, in some embodiments the distal hub may be in the form of the catheter tip 92 which distally abuts the proximal collar 30 and/or proximal waist 20 thereby preventing longitudinal migration of the balloon 16 in the distal direction.

Figure 8:
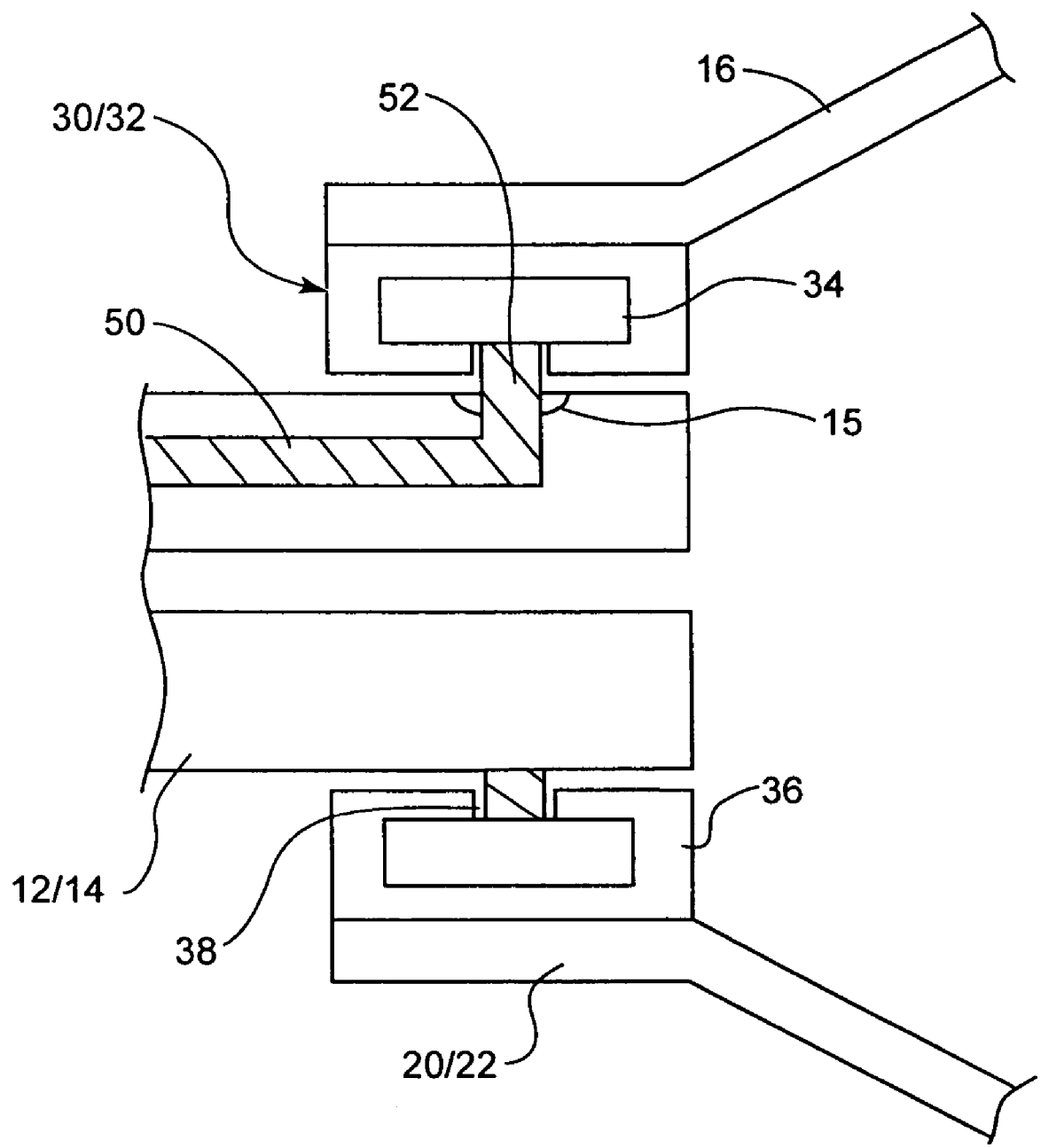
FIG. 8 is an enlarged partial side view of a collar such as may be utilized by the embodiment shown in FIG. 1 shown prior to exposure to an electric current.
Figure 9:
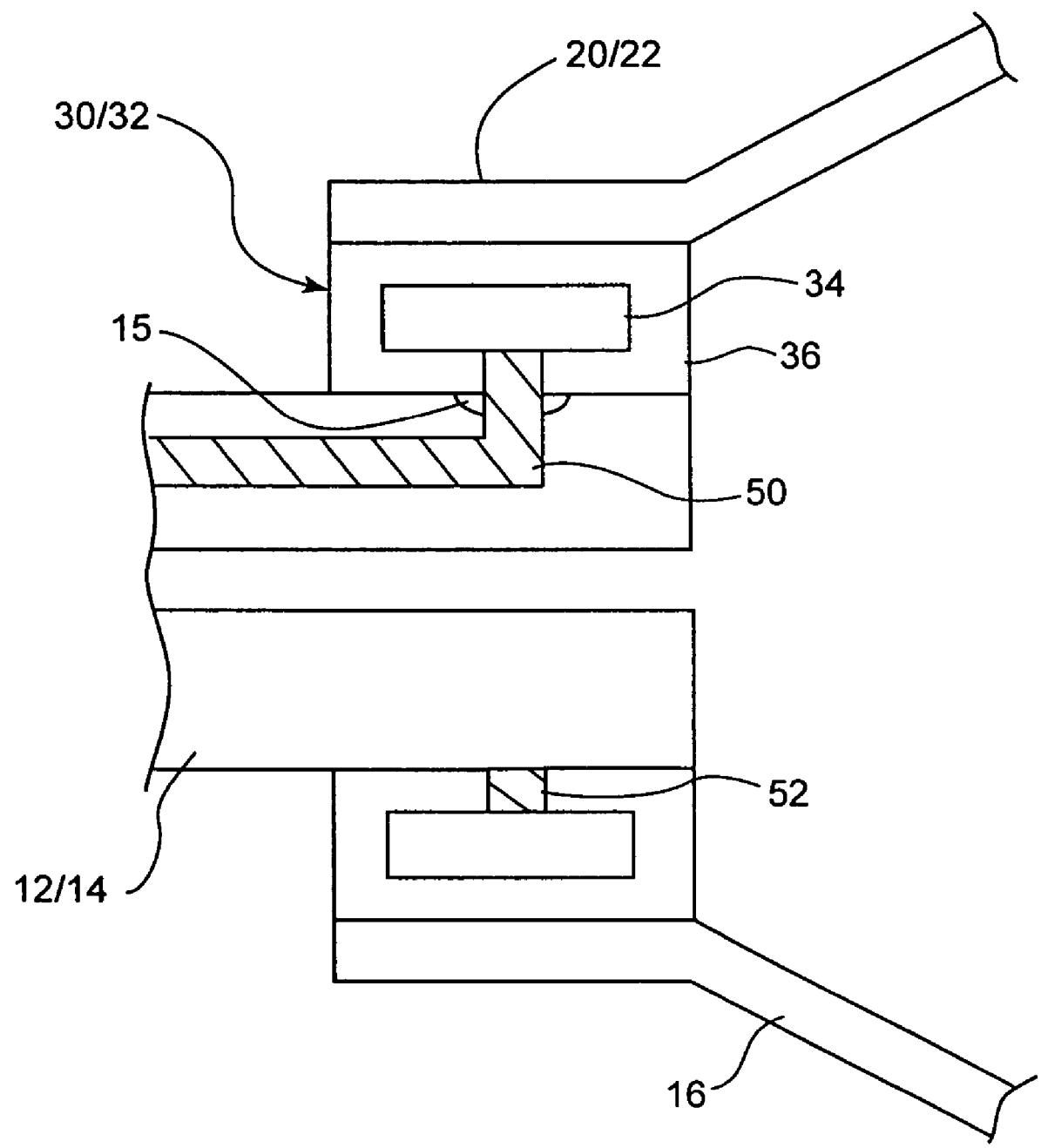
FIG. 9 is an enlarged partial side view of the collar illustrated in FIG. 8 shown during exposure to an electric current.

In some embodiments where the collars 30 and 32 are rotatable about the catheter shaft in the pre-current state, in some cases the collars 30 and 32 may avoid the need for hubs by rotatably disposing the collars 30 and/or 32 to a conductive ring 52 such as in the manner depicted in FIGS. 8 and 9. In the embodiment shown in FIGS. 8 and 9 the conductive wire 50 may further comprise a conductive ring 52 which projects radially outward from the catheter shaft 12/14. The EAP layer 36 and/or the marker 34 of a collar 30/32 may define a grove or track 38 which is rotatably engaged to the ring 52 prior to exposure of the collar to the electric current. When current 62 is supplied to the ring 52, and thus the collar 30/32 as well, the layer 36 of EAP material will expand to close the grove against the ring 52 and seal the collar 30/32 about the shaft 12/14.

In the various embodiments shown in FIGS. 2-5, prior to electric activation of the collars 30 and 32, the balloon 16 is freely rotatable about the catheter shafts 12 and 14. This capacity to freely rotate allows a stent 70 mounted on the balloon 16 to be rotationally oriented within a body vessel 100 during advancement of the assembly 10 without necessitating torquing of the catheter shafts 12 and/or 14. Because the balloon 16 is freely rotatable, it is desirable to provide the balloon 16 with a mechanism which allows the balloon 16 to be rotated to a desired position.

In the various embodiments described herein the catheter assembly 10 may be a fixed wire catheter or any other catheter design. In the embodiment depicted in FIGS. 1-5 for example the catheter is an over the wire design wherein the inner shaft 12 defines a primary guidewire lumen 11 along which a primary guidewire 13 may be advanced.

In some embodiments, such as are illustrated in FIGS. 1-5, such a mechanism is comprised of a secondary guidewire housing 80. Housing 80 may be comprised of an tubular member which defines a secondary guidewire lumen 84 through which a secondary guidewire 86 may be advanced. The housing 80 is engaged to the balloon 16 or defined by the balloon wall as desired. The housing 80 may be comprised of one or more tubular members 82. Where multiple members 82 are included in the housing 80, the members are disposed about one another to provide the housing with a variety of flexibility, hardness, and/or stiffness characteristics as desired. As such the housing 80 may be constructed of any of a wide variety of materials including metal(s), polymer(s), natural rubber, silicone, multilayer materials, urethanes, Pebax, HDPE, etc.

When the stent 70 is properly positioned on the balloon 16, such as in the manner depicted in FIGS. 1-5, a proximal portion 72 of the stent 70 is also disposed about at least a portion of the secondary guidewire housing 80. When the stent 70 is thusly positioned about the balloon 16 and the housing 80, in some embodiments, such as for example that shown in FIGS. 10 and 11, at least a portion of the housing 80 and/or the secondary guidewire 86 extends distally through a cell opening 76 of the stent 70.

Figure 10:
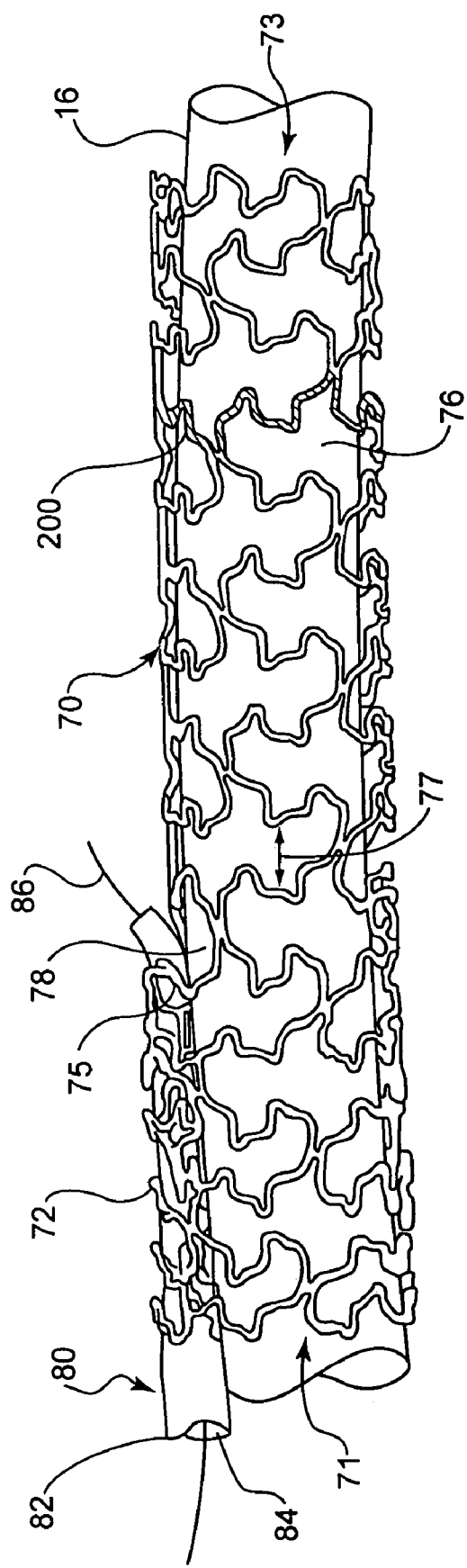
FIG. 10 is a partial side view of the balloon shown in FIG. 1 with a stent and guidewire housing shown engaged thereto.
Figure 11:
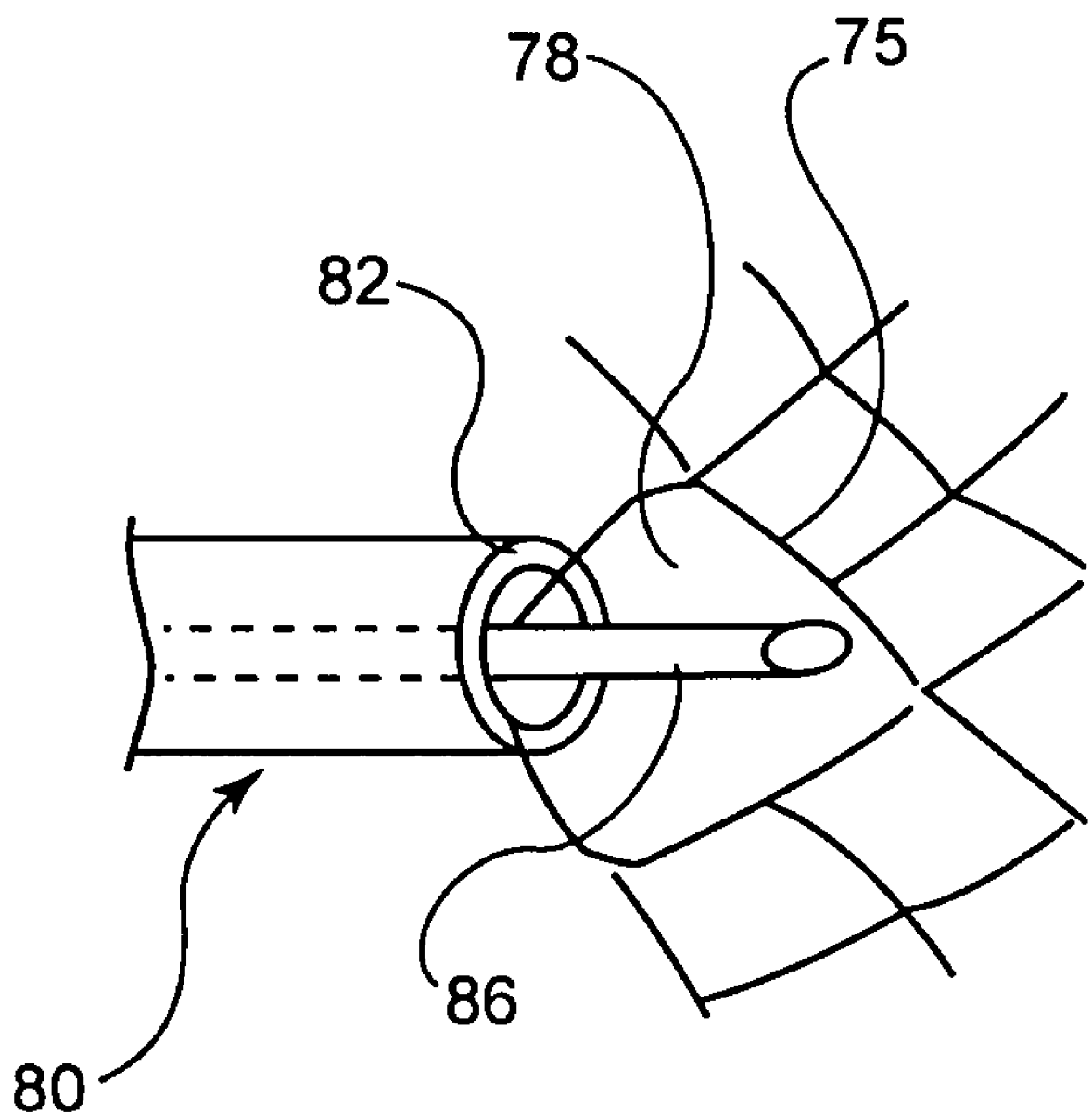
FIG. 11 is a close up view of a secondary opening of a region of the assembly shown in FIG. 1.

Stent 70 may be a stent, such as is shown in FIG. 10, which is at least partially constructed of a plurality of interconnected struts, connectors or members 75. The stent 70 defines a proximal opening 71, a distal opening 73 and a flow path 77 there between. The cell openings 76 are in fluid communication with the flow path 77.

When the secondary guidewire 86 and/or the secondary guidewire housing 80 is threaded through one of the cell openings 76 when the stent is positioned onto the assembly 10, such as is shown in FIG. 1, and 10-12, the members 75 that define the selected cell opening 78, as well as the shape of the opening 78 through which the secondary guidewire 86 exits the stent, may be distorted or modified in order to accommodate the passage of secondary guidewire 86 and/or the secondary guidewire housing 80 there through.

Figure 12:
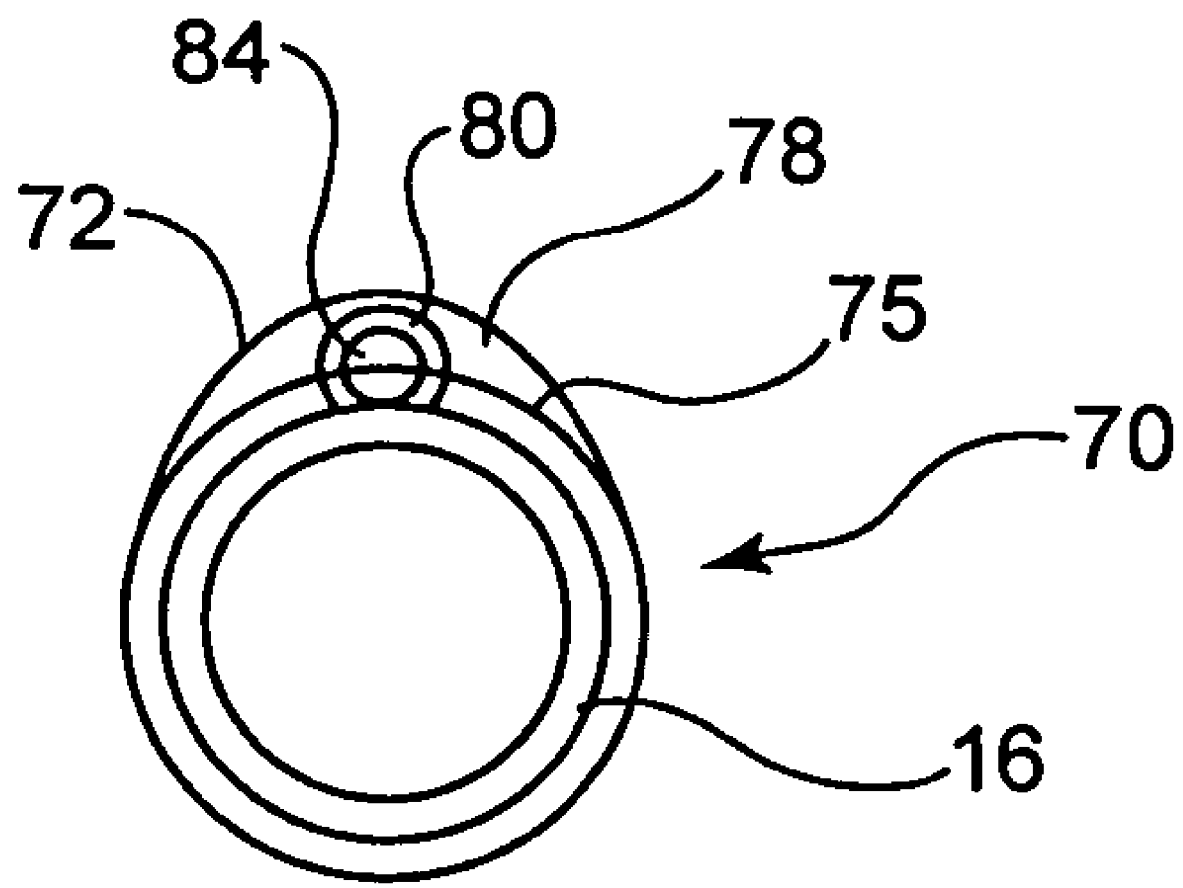
FIG. 12 is a cross sectional view of the balloon shown in FIG. 10.

This modified cell opening 78, hereinafter referred to as secondary opening 78, is positioned on the stent 70 between the proximal opening 71 and the distal opening 73. The manner in which the secondary opening 78, the members 75 adjacent thereto, and to an extent the stent 70 itself, are modified or distorted by the position of the secondary guidewire and/or secondary guidewire housing is best illustrated in FIGS. 10 and 12.

It should be noted that when the stent 70 is placed on the balloon 16 in the manner described above, the distortion of the secondary opening 78 and the adjacent members 75 may be of a minimal nature providing only a sufficient alteration to the cell to allow sliding passage of the secondary guidewire 86, and if desired a distal portion of the secondary guidewire housing 80 there through. As such, the actual size of the secondary opening 78 may be substantially similar, or only marginally different than that of the surrounding cell openings 76.

It should also be further noted that while stent 70 may be a standard "single vessel" stent that is provided with a secondary opening 78 in the manner described above, the stent 70 may also be a bifurcated stent having a trunk and/or stem portion, with one or more leg portions and/or branch openings adjacent thereto, through which the secondary guidewire may be passed. Such bifurcated stents and stent assemblies are well known in the art.

In some embodiments, the secondary guidewire 86 is merely slid between the balloon 16 and the stent 70 without the use of a housing 80. In some embodiments, where the stent 70 is to be positioned substantially proximal to a side branch of the bifurcation, the guidewire 86 and/or housing 80 may be configured to extend under the entire length of the stent 70.

Figure 13:
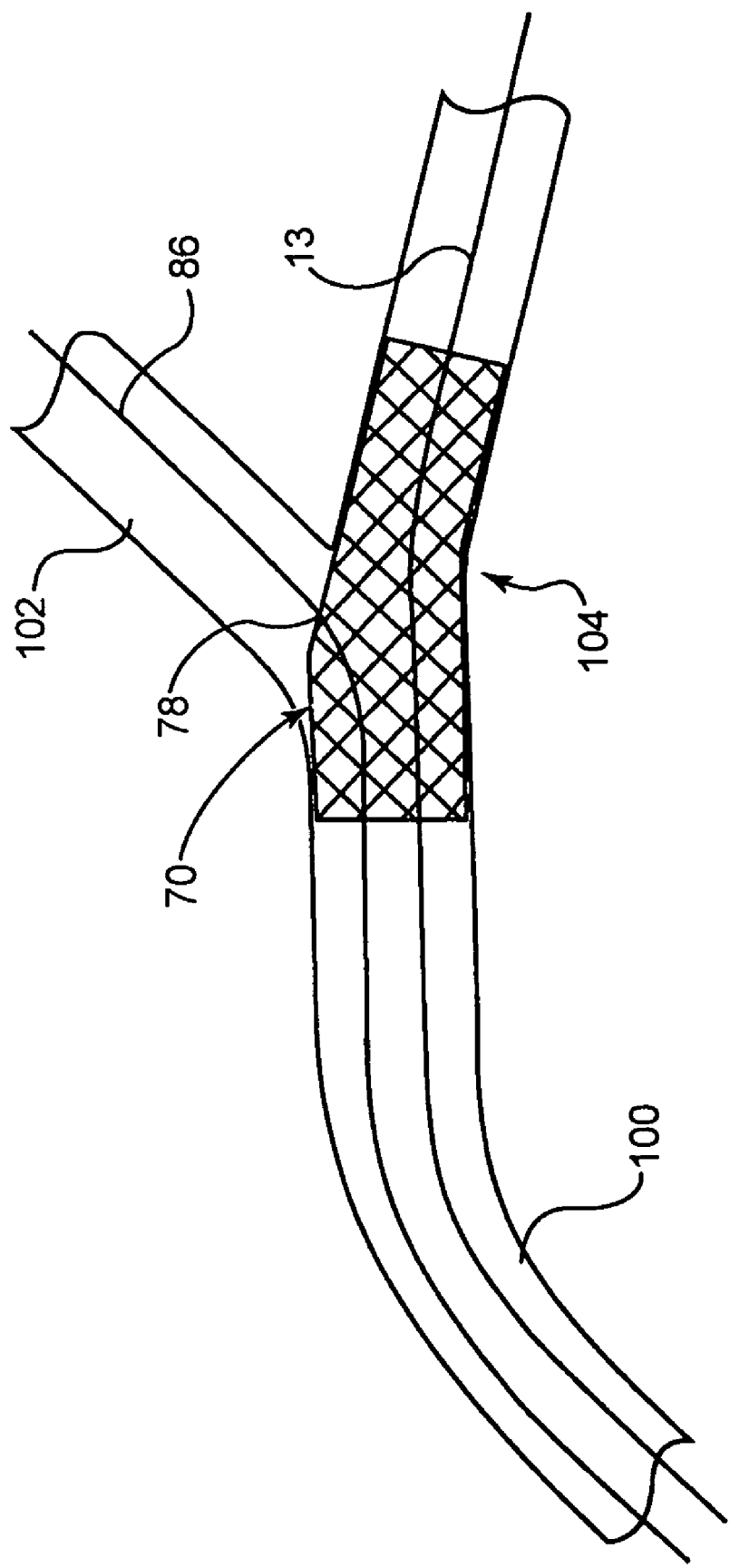
FIG. 13 is a longitudinal cross-sectional view of the stent depicted in FIGS. 10-12 shown after delivery and withdrawal of the catheter assembly.

In operation, the secondary guidewire 86 is initially advanced through the vessel 100 and into a side branch 102 of a bifurcation 104. By advancing the catheter assembly 10 along the secondary guidewire 86 in the manner described above, the balloon 16 and the stent 70 disposed thereabout will be rotated to align the secondary opening 78 of the stent 70 with the side branch vessel 102. Once properly positioned in this manner the collars 30 and 32 may be activated and the balloon 16 expanded to deliver the stent 70 such as in the manner depicted in FIGS. 3 and 5. As shown in FIG. 13, once the stent 70 is delivered the balloon is deflated and the assembly is withdrawn from the vessel 100.

In some cases, the stent 70, or one or more portions of the assembly 10 thereof, may be configured to deliver one or more therapeutic agents to a delivery site within the vessel 100 or one or more areas adjacent thereto such as shown in FIGS. 2-5.

To better accommodate placement of a therapeutic agent on the stent 70, in some instances one or more stent members 75, such as is shown in FIG. 10, maybe configured to include one or more holes, notches, or other surface features to which one or more therapeutic agents 200 may be placed for delivery to the aneurysm site. A therapeutic agent may be placed on the stent in the form of a coating. Often the coating includes at least one therapeutic agent and at least one polymer.

A therapeutic agent may be a drug, a non-genetic agent, a genetic agent, etc. Some examples of suitable non-genetic therapeutic agents include but a re not limited to: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vascoactive mechanisms, and any combinations thereof.

Where an agent includes a genetic therapeutic agent, such a genetic agent may include but is not limited to: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

Where a therapeutic includes cellular material, the cellular material may include but is not limited to: cells of human origin (autologous or allogeneic); cells of non-human origin (xenogeneic) and any combination thereof. Some examples of cellular material include but are not limited to the following:

SP—(side population cells) These cells are thought to be some of the most primitive adult stem cells. They are isolated by a specific FACS technique utilizing the ability of SP cells to exclude Hoechst dye from the nucleus. In addition to bone marrow, SP cells have been isolated from most tissues, including: cardiac and skeletal muscle. By the more common surface protein identification these cells are $Lin^-$, $Sca-1^+$, $c-Kit^+$, $CD43^+$, $CD45^+$, $CD34^-$ Lin⁻—(lineage negative cells) This group of cells is isolated from the bone marrow and all cells which have differentiated to a specific lineage (e.g. red blood cells) have been removed. Therefore leaving all of the stem and progenitor cells. This is beneficial because all primitive cells remain, but may reduce efficiency by including irrelevant, primitive cell types.

$Lin^-CD34^-$—Although $CD34^+$ cells have received much attention, many articles have been published lately which suggest the most primitive bone marrow derived stem cells are $CD34^-$ $Lin^-CD34^+$—Presence of the cell surface protein CD34 has been used to identify hematopoietic stem cells. However, the marker is also present on progenitor cells and white blood cells of various levels of maturity.

$Lin^-cKit^+$—cKit is the cell surface receptor for stem cell factor, and therefore a logical choice for stem cell selection. Most widely studied from bone marrow sources, but have also been isolated from the heart.

MSC—(mesenchymal stem cells) Named so because ordinarily these cells differentiate into cells of mesenchymal tissues (e.g. bone, cartilage, fat), but may also differentiate into cardiomyocytes under certain conditions. Easily isolated from bone marrow and, unlike hematopoietic stem cells, proliferate in vitro. A subpopulation of MSCs has been shown to self-renew faster and have a greater potential for multipotential differentiation than the general MSC population. D. Prockop from Tulane U. is publishing in this area.

Cord Blood Cells—Derived from the blood remaining in the umbilical vein following child birth. This blood has been shown to contain a higher percentage of immature stem cells or progenitor cells. Typically, a matched donor must be found for patients, but a lower incidence of graft versus host disease compared to stem cell isolation from adult blood has been reported. Disadvantages include: insufficient cell number in small blood volumes, unforeseen congenital defects, and contamination by mother's blood which is likely not HLA matched.

Cardiac or other tissue derived stem cells—Most work to date has focused on isolating stem cells from bone marrow. This is due to extensive work in improving bone marrow transplants for chemotherapy and leukemia treatments. However, there is evidence that similar stem cells which can be identified by similar means (e.g. SP, cKit) can be isolated from other tissues (e.g. fat, cardiac muscle).

Whole bone marrow—An "it's in there" approach where whole bone marrow (filtered for bone particles) is transplanted. Benefits include: little processing, all stem and progenitor cells are present, and matrix proteins and growth factors may also be present. Downside—if one or two stem cell types are responsible for cardiac improvement they will only be present in very low numbers.

BM-MNCs—(bone marrow mononuclear cells) Separated from whole bone marrow by a density gradient centrifugation procedure, this population contains non-granular white blood cells, progenitor cells, and stem cells.

EPCs—(endothelial progenitor cells) Isolated from bone marrow based on cell surface markers, these cells will become endothelial cells. In theory, these cells will form new blood vessels when delivered to ischemic tissue.

Skeletal myoblasts—(or satellite cells) These cells are responsible for the regeneration of skeletal muscle following injury. They have the ability to fuse with other myoblasts or damaged muscle fibers. Cardiac muscle therapies assume these cells can integrate into the host tissue and improve tissue properties or functionally participate in contraction.

MDCs—(muscle derived cells) A population of cells isolated from adult skeletal muscle which are similar to myoblasts. The isolation technique preplating entails collecting cells which attach to culture dishes at different times after biopsy. Cells with the best potential plate in the $6^{th}$ group and takes several days to obtain. Investigators working with these cells claim they are a refined population of myoblasts and should result in higher engraftment efficiencies and efficacious procedures.

Go cells—Recently isolated from adult skeletal muscle, these non-satellite cells express GATA-4 and, under certain in vitro growth conditions, progress to spontaneously beating cardiomyocyte-like cells.

Endothelial cells—Transplantation of autologous endothelial cells along with a fibrin matrix induced angiogenesis and improved cardiac function in an ischemic sheep model.

Adult Cardiomyocytes

Fibroblasts—Easily obtained from adult tissues, fibroblasts may provide growth factors or participate in the would healing response. Fibroblast play a critical role in wound healing; the synthesis and deposition of extracellular matrix. Fibroblasts commonly become contractile in wound healing environments.

Smooth muscle cells—Isolated from arteries, these cells may participate or encourage angiogenesis and/or beneficial cardiac remodeling following MI.

MSCs+5-aza—Culture of mesenchymal stem cells with 5-aza forces differentiation into cardiomyocytes. These cells beat spontaneously after treatment.

Adult cardiac fibroblasts+5-aza—In theory, in vitro treatment of cardiac fibroblasts with 5-aza will result in differentiation into myogenic cells.

Genetically modified cells—Isolation of cells from the patient and genetically modifying them in vitro to encourage production of proteins or differentiation into a cell type which will be beneficial for treating heart failure.

Tissue engineered grafts—Isolation of cells from the patient which are then seeded onto and cultured within resorbable scaffolds (e.g. collagen, PLGA). These cell seeded constructs are then implanted into the patient.

MyoD scar fibroblasts—MyoD family of transcription factors prompt skeletal muscle cell differentiation in fibroblasts. Procedure involves isolation of cardiac scar fibroblasts, genetic transfection with MyoD in vitro and delivery of the cells to the heart to encourage myogenesis.

Pacing cells—Genetically modified fibroblasts which become electrically conducting and signal generators.

Embryonic stem cell clones—Use of cloning technology to produce cardiomyocytes, progenitors, or stem cells which are genetically identical to the patient.

Embryonic stem cells—These cells are the most primitive of cells and will differentiate into functional cardiomyocytes under certain conditions. Both political and technological hurdles must be overcome before commercialization of this technology.

Fetal or neonatal cells—Isolated from the heart of donors, these cells may incorporate into host tissue without immune rejection. Some cardiomyocyte progenitor cells must be present due to the continued growth of the heart in fetal and neonatal humans.

Immunologically masked cells—Allogeneic cell sources (e.g. donor cardiomyocytes) are currently unfeasible due to immune rejection. However, masking technologies have been developed which could make this technology feasible.

Tissue engineered grafts—Isolation of cells from a donor which are then seeded onto and cultured within resorbable scaffolds (e.g. collagen, PLGA). These cell seeded constructs are then implanted into the host or recipient.

Genetically modified cells—Isolation of cells from a donor and genetically modifying them in vitro to encourage production of proteins or differentiation into a cell type which will be beneficial for treating heart failure. The modified cells will then be transplanted into the host or patient.

Teratoma derived cells—A teratocarcinoma is a form of cancer in which the tumor is composed of a heterogeneous mixture of tissues. Through isolation of cells from this tumor and in vitro manipulation and culture a neuronal cell line has been developed. Layton Biosciences has successfully used these cells to form new brain tissue in stroke patients. Similar techniques may be used to produce a myogenic cell line.

Where a therapeutic agent comprises at least one polymer agent or coating, the at least one coating may include but is not limited to: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.), fibrin, collagen and derivatives thereof; polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$_4$'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; and any combinations thereof.

In some instances a suitable polymer agent or coating comprises block copolymers comprising at least one A block and at least one B block. The A blocks are preferably soft elastomeric blocks, which are based upon one or more polyolefins, or other polymer with a glass transition temperature at or below room temperature. For example, the A blocks can be polyolefinic blocks having alternating quaternary and secondary carbons of the general formulation: —(CRR'—CH$_2$)$_n$—, where R and R' are, independently, linear or branched aliphatic groups such as methyl, ethyl, propyl, isopropyl, butyl, isobutyl and so forth, or represent cyclic aliphatic groups such as cyclohexane, cyclopentane, and the like, either with or without pendant groups. Preferred polyolefinic blocks include polymeric blocks of isobutylene,

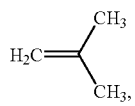

(i.e., polymers where R and R' are methyl groups). Other examples of A blocks include silicone rubber blocks and acrylate rubber blocks.

The B blocks are preferably hard thermoplastic blocks with glass transition temperatures significantly higher than the elastomeric A blocks which, when combined with the soft A blocks, are capable of, inter alia, altering or adjusting the hardness of the resulting copolymer to achieve a desired combination of qualities. Examples of B blocks include polymers of methacrylates or polymers of vinyl aromatics. More specific examples of B blocks include blocks that are (a) formed from monomers of styrene

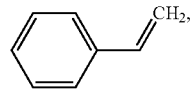

styrene derivatives (e.g., x-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks" or are (b) formed from monomers of methylmethacrylate, ethylmethacrylate, hydroxyethyl methacrylate or mixtures of the same.

The block copolymers are provided in a variety of architectures, including cyclic, linear, and branched architectures. Branched architectures include star-shaped architectures (e.g., architectures in which three or more chains emanate from a single region), comb architectures (e.g., copolymers having a main chain and a plurality of side chains), and dendritic architectures (including arborescent or hyperbranched copolymers).

Some specific examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X-(BA)$_n$ (includes diblock, triblock and other radial block copolymers), where n is a positive whole number and X is a starting seed, or initiator, molecule. One specific group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block, with the triblock therefore denoted as BAB). A particularly beneficial polymer from this group is polystyrene-polyisobutylene-polystyrene triblock copolymer (SIBS). Where n=3 or more, these structures are commonly referred to as star-shaped block copolymers. Other examples of block polymers include branched block copolymers such as dendritic block copolymers, wherein at least one of the A and B blocks is branched, for instance, where the A blocks are branched and are capped by the B blocks.

Figure 14:
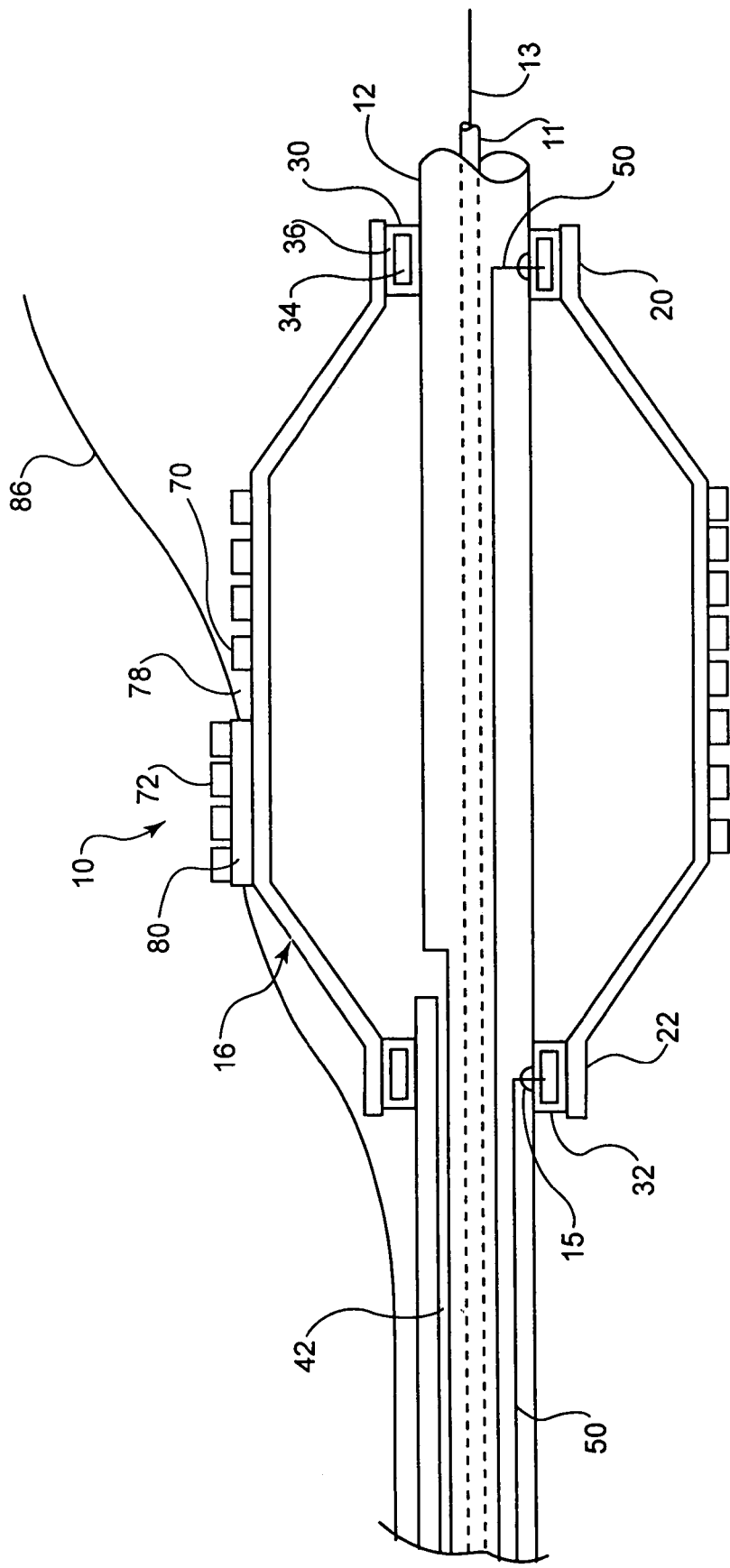
FIG. 14 is a longitudinal cross-sectional view of an embodiment of the invention wherein the catheter assembly comprises a single catheter shaft.

In the embodiment shown in FIGS. 1-5 the assembly 10 comprises an inner shaft 12 and an outer shaft 14 with respective ends of the balloon 16 rotatable thereabout. It is noted however, that in some embodiments the catheter assembly 10 may include a single or inner catheter shaft 12, such as in the embodiment depicted in FIG. 14 for example, wherein both collars 30 and 32 are disposed about the same shaft 12. Collars 30 and 32 may be rotatable or fixedly engaged to the shaft 12 in the same or similar manners as have been previously described. The balloon 16, prior to activation of the EAP material in the collars 30 and 32, is thus rotatable about the single catheter shaft 12. The shaft 12 may be molded or extruded to include an inflation lumen 42 for inflation of the balloon 16 following electrical activation of the collars 30 and 32.

It may be recognized that in order for the collars 30 and 32 to be electrically activated to trigger the expansion of the EAP material therein, an electric circuit necessarily needs to be formed between the conductive member 50, the current source 60, and each collar 30 and 32. It will be recognized however that the presence of saline (e.g. within bodily fluid such as blood, etc.) within the vessel and/or the balloon interior 40 during inflation completes the circuit to allow the current to flow to the collars as desired.

Figure 15:
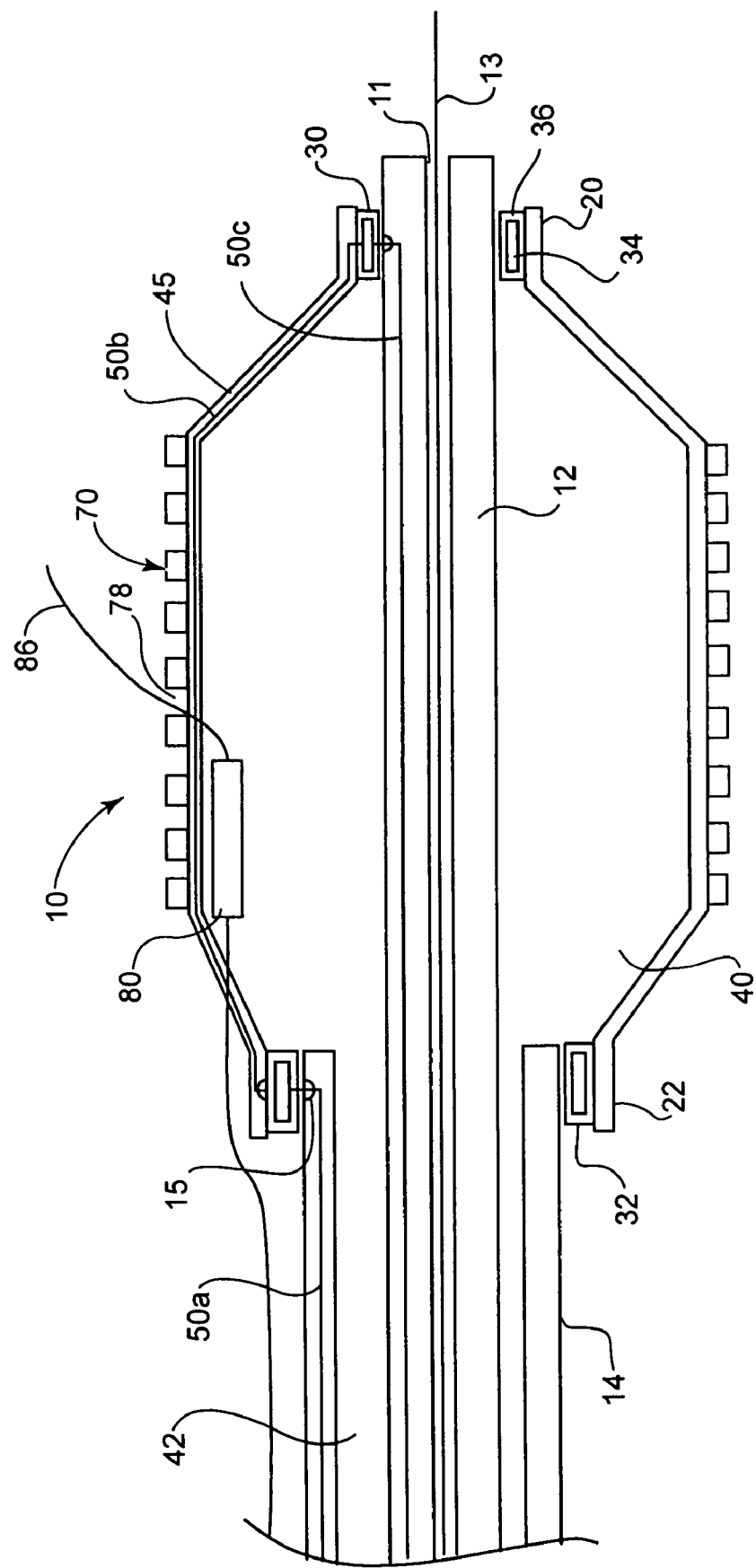
FIG. 15 is a longitudinal cross-sectional view of an embodiment of the invention wherein the balloon wall comprises a conductive member is conductive communication with the proximal and distal collars.

However, in some embodiments the formation of such a circuit may be a function of the assembly 10 alone. For example in the embodiment shown in FIG. 15, a first conductive wire 50a is contained within the outer shaft 14 or within the inflation lumen 42. Wire 50a extends from the current source 60 (shown in FIG. 6) to the proximal collar 32 and provides electrical communication there between. An intermediate conductive member or wire 50b extends through the wall 45 of the balloon or alternatively through the balloon interior 40 and is in communication between the collars 32 and 30. A third or interior conductive member 50c extends through the inner shaft 12 and is in communication with the distal collar 30 and extends proximally back to the current source 60 (shown in FIG. 6) to complete the circuit.

As indicated above the collars 30 and 32 may be engaged to the balloon 16, and more particularly to the respective waists 20 and 22 of the balloon 16 in a variety of manners. Some examples of such engagement are illustrated in FIGS. 16-19.

Figure 16:
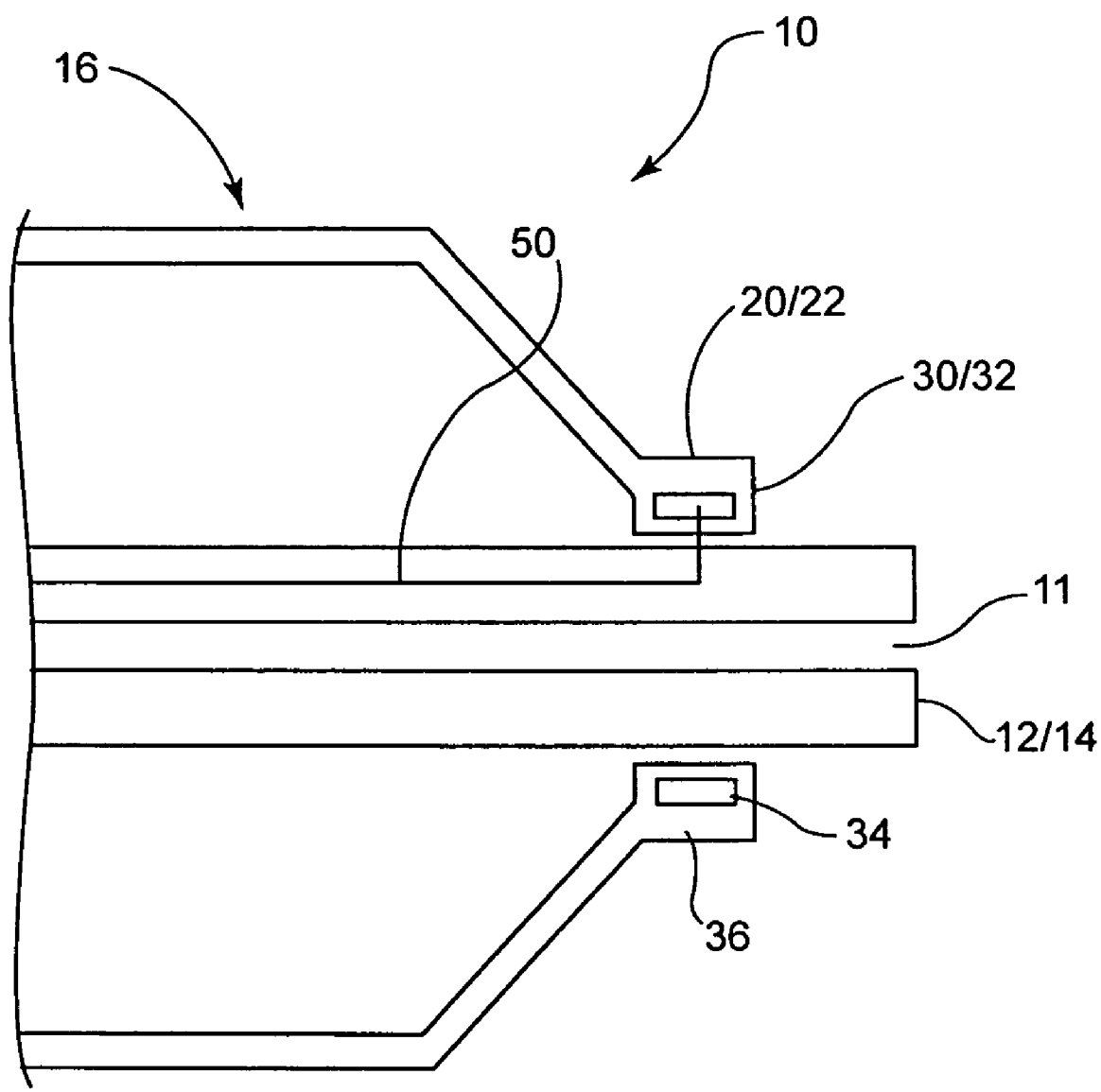
FIG. 16 is a partial view of a catheter assembly showing an optional engagement configuration between the balloon waist and the collar.

In the embodiment shown in FIG. 16 the collar 30/32 is integral with the balloon waist 20/22. In this embodiment the collar 30/32 is extruded or co-extruded with the balloon 16. In some embodiments marker 34 may likewise be co-extruded or may be subsequently secured to the structure.

Figure 17:
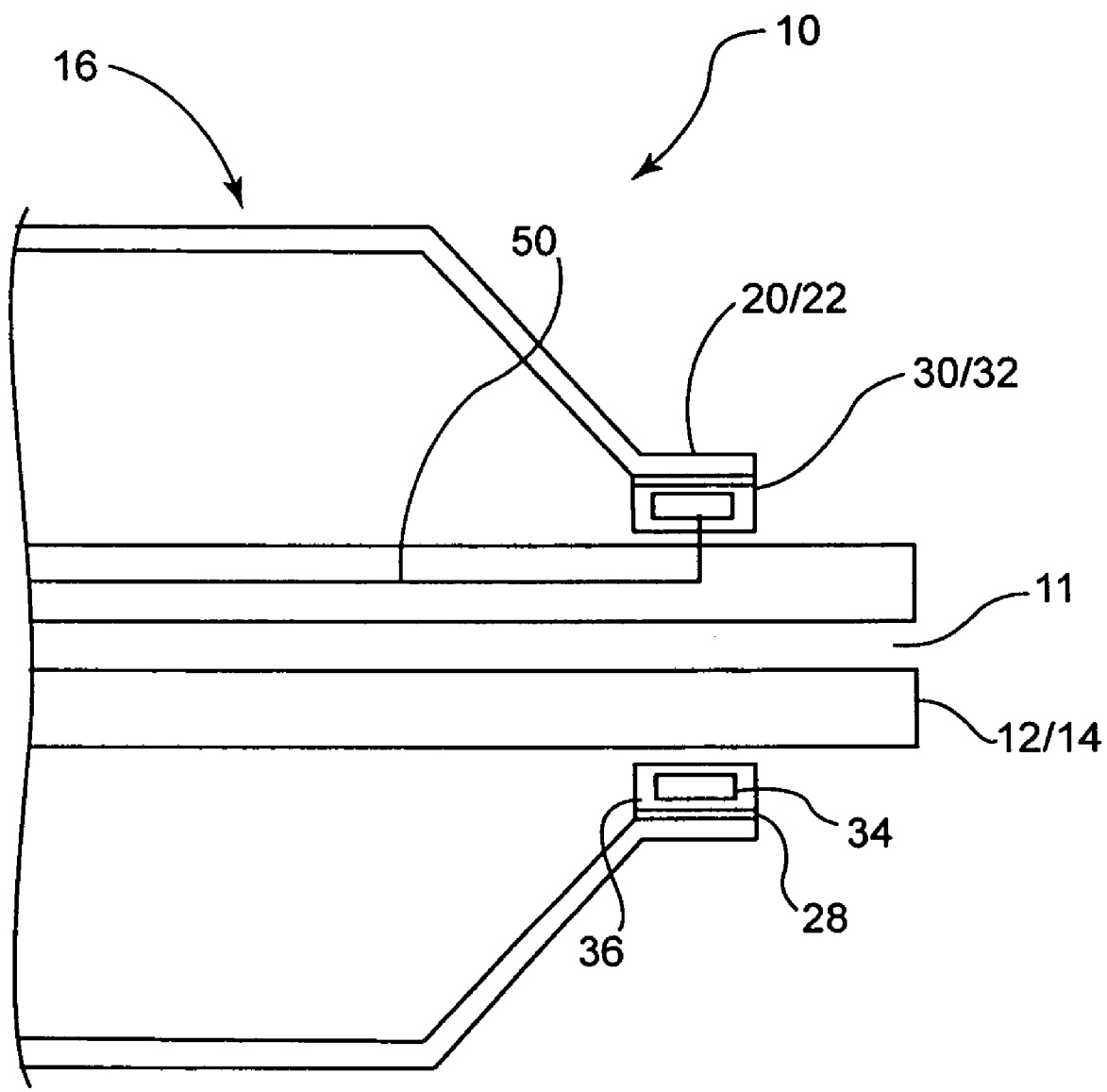
FIG. 17 is a partial view of a catheter assembly showing an optional engagement configuration between the balloon waist and the collar.
Figure 19:
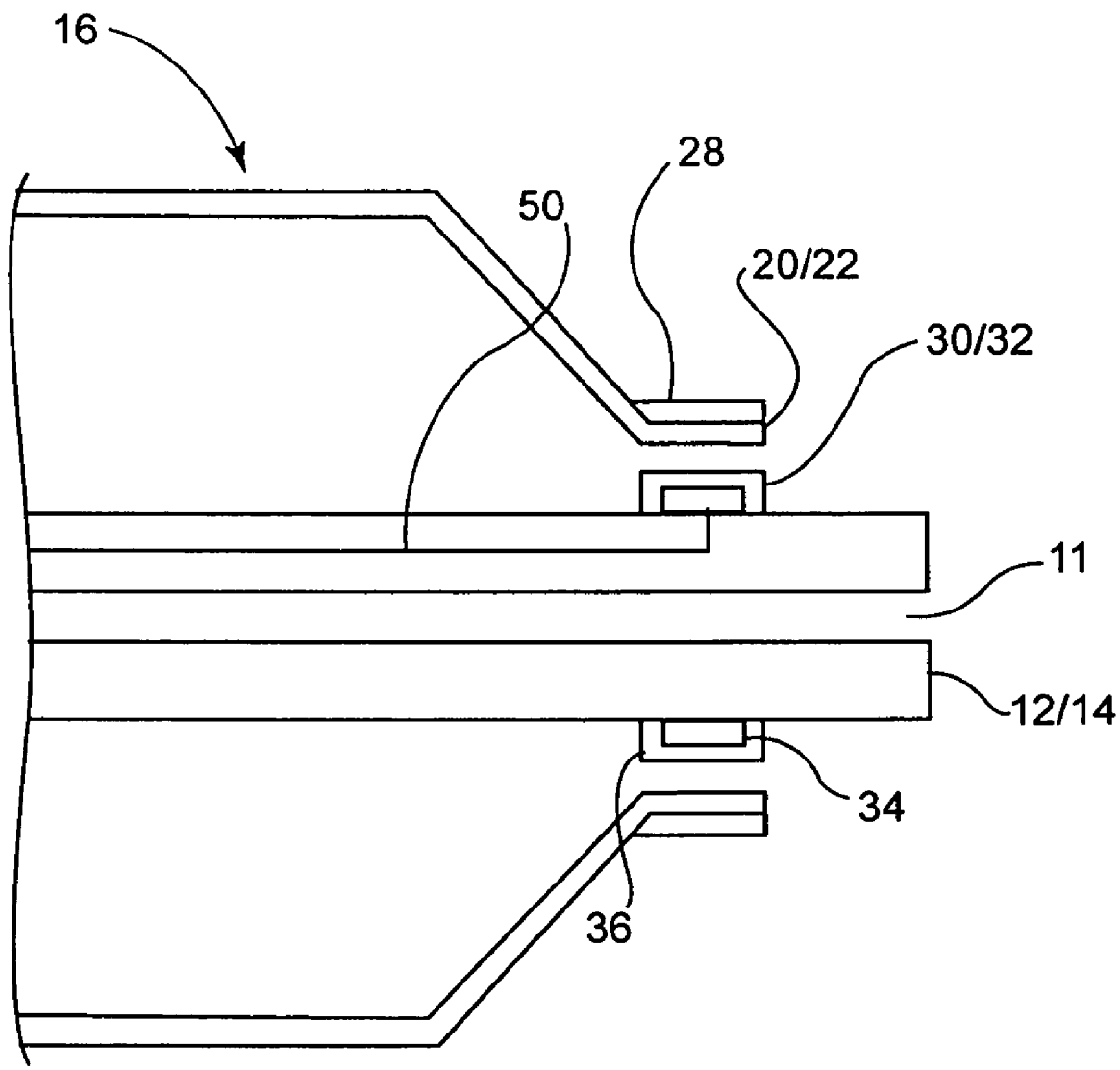
FIG. 19 is a partial view of a catheter assembly showing an optional engagement configuration between the catheter shaft and the collar.

In some embodiments, such as in the example shown in FIGS. 17 and 19 it may be desirable to reinforce the waist 20/22 of the balloon 16. In at least one embodiment the waist 20/22 may be supplemented with one or more layers 28 of transition material. Where the transition material 28 is external to the waist 20/22 as in the embodiment shown in FIG. 19, the layer 28 may reinforce the waist to help insure the fluid tightness of the balloon seal in the pre-current state and to improve the rotational characteristics of the balloon 16. In such an embodiment the layer 28 may be constructed of one or more strands fibers or layers of stainless steel or other suitable reinforcing material In embodiments where the waist 20/22 is engaged to the collar 30.32 in the pre-current state, such as in FIG. 17the transition material layer 28 may aid in bonding the material of the waist 20/22 to the material of the collar 30/32. Some examples of suitable transition materials for forming the layer 28 include but are not limited to: Plexar, Selar, EMS Hytrel, etc.

Figure 18:
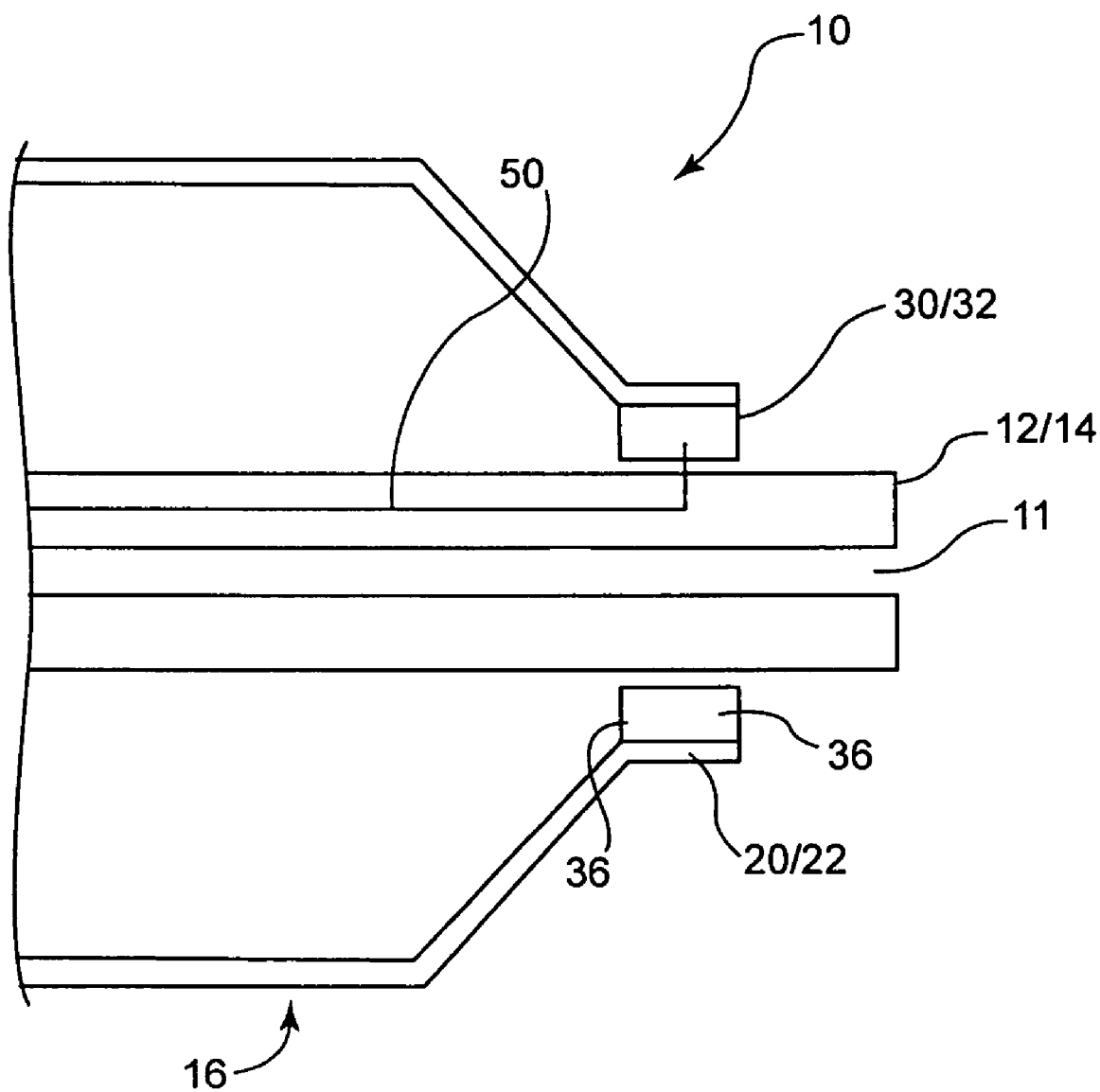
FIG. 18 is a partial view of a catheter assembly showing an optional engagement configuration between the balloon waist and the collar.

In some embodiments, such as in the example shown in FIG. 18, the use of a marker such as previously described may be unnecessary. As such a collar 30/32 of EAP may be directly welded or otherwise engaged to the waist 20/22 or in the alternative to the shaft 12/14.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

With this description, those skilled in the art may recognize other equivalents to the specific embodiment described herein. Such equivalents are intended to be encompassed by the claims attached hereto.

The invention claimed is:

1. A catheter assembly comprising:
   a catheter shaft, the catheter shaft having a length and an outer surface;
   a balloon, the balloon comprising a proximal balloon waist, a distal balloon waist and a body portion therebetween, the balloon having an expanded state and a unexpanded state, in the expanded state the body portion having an expanded diameter and in the unexpanded state the body portion having an unexpanded diameter that is less than the expanded diameter; and
   a proximal collar and a distal collar, the proximal collar fixed to the catheter shaft and the distal collar fixed to the catheter shaft, each collar having a nonactivated state and an activated state, in the nonactivated state the distal balloon waist being rotatable about the distal collar and the proximal balloon waist being rotatable about the proximal collar, in the activated state the proximal collar being expanded to sealingly engage the proximal balloon waist and the distal collar being expanded to sealingly engage the distal balloon waist.

2. The catheter assembly of claim 1 wherein the collars are actuated between the nonactivated state and the activated state by exposure to an electric current.

3. The catheter assembly of claim 2 further comprising at least one electrically conductive member, each collar being in electronic communication with the at least one electrically conductive member.

4. The catheter assembly of claim 3 further comprising a source of electrical current, the source being in electronic communication with the at least one electrically conductive member.

5. The catheter assembly of claim 4 wherein the catheter shaft comprises an inner catheter shaft and an outer catheter shaft, the proximal collar being engaged to a portion of the outer catheter shaft and the distal collar being engaged to a portion of the inner catheter shaft.

6. The catheter assembly of claim 5 wherein the inner catheter shaft is at least partially constructed of at least one material of the group consisting of: HDPE, Pebax, Polyamide, Nylon, multilayer extrusions and any combination thereof.

7. The catheter assembly of claim 6 wherein the at least one electrically conductive member is at least partially enclosed by the inner catheter shaft.

8. The catheter assembly of claim 7 wherein the at least one electrically conductive member is co-extruded with the at least one material of the inner catheter shaft.

9. The catheter assembly of claim 7 wherein the support ring is at least partially constructed of at least one material of the group consisting of: stainless steel, Nitinol, acetyl, PI, HDPE, LX2/TR55, nanocomposites, ceramics, and any combinations thereof.

10. The catheter assembly of claim 5 wherein the outer catheter shaft is at least partially constructed of at least one material of the group consisting of: Pebax, Nylon, nanocompostites, multilayer extrusions, and any combination thereof.

11. The catheter assembly of claim 10 wherein the at least one electrically conductive member is at least partially enclosed by the outer catheter shaft.

12. The catheter assembly of claim 11 wherein the at least one electrically conductive member is co-extruded with the at least one material of the outer catheter shaft.

13. The catheter assembly of claim 5 wherein the outer catheter shaft is disposed about a portion of the inner catheter shaft, an inflation lumen in fluid communication with an interior of the balloon body being defined by a space between the inner catheter shaft and the outer catheter shaft.

14. The catheter assembly of claim 13 wherein the portion of the outer catheter shaft is disposed about a support ring, the inner catheter shaft extending through the support ring.

15. The catheter assembly of claim 4 further comprising an inflation fluid, the inflation fluid being injected into the balloon in order to expand the balloon from the unexpanded state to the expanded state, the inflation fluid being electrically conductive.

16. The catheter assembly of claim 15 wherein the proximal collar, the distal collar, the at least one electrically conductive member, the inflation fluid and the source of electric current forming an electric circuit through which the electric current flows to place the collars in the activated state.

17. The catheter assembly of claim 3 wherein the at least one electrically conductive member is at least partially constructed of at least one material of the group consisting of: gold, silver, platinum, nitinol, and any combination thereof.

18. The catheter assembly of claim 3 wherein the at least one conductive member is positioned within at least a portion of the balloon.

19. The catheter assembly of claim 18 wherein the at least one electrically conductive member is co-extruded within the at least a portion of the balloon.

20. The catheter assembly of claim 3 wherein the proximal collar and the distal collar are comprised of electro-active polymer (EAP) material.

21. The catheter assembly of claim 20 wherein the EAP material is selected from at least one member of the group consisting of: Poly-pyrrole (PPY), Poly-Aniline (PAni), Poly-Thiofene (PTH), Poly-Paraphenylene Vinylene (PPV), Nation, Bucky paper, and any combination thereof.

22. The catheter assembly of claim 20 wherein when the proximal collar and the distal collar are exposed to the electric current the EAP material in each collar expands about 0.5% to about 20 percent.

23. The catheter assembly of claim 20 wherein the proximal collar and the distal collar are further comprised of at least one electrically conductive marker, the EAP material being a layer of material engaged to at least a portion of a surface of the at least one electrically conductive marker.

24. The catheter assembly of claim 23 wherein the at least one electrically conductive marker is constructed of at least one material of the group consisting of gold, platinum, silver, nitinol, and any combination thereof.

25. The catheter assembly of claim 24 wherein the at least one electrically conductive marker is in direct contact with a portion of the at least one electrically conductive member which radially extends through at least one opening in the catheter shaft.

26. The catheter assembly of claim 1 further comprising at least one marker band the at least one marker band being engaged to a portion of the catheter shaft.

27. The catheter assembly of claim 26 wherein the at least one marker band is at least partially radiopaque.

28. The catheter assembly of claim 26 wherein the at least one marker band is detectable by at least one imaging modality selected from the group consisting of X-Ray, MRI ultrasound and a combination thereof.

29. The catheter assembly of claim 1 wherein the balloon is constructed of at least one member of the group consisting of: Pebax, Nylon, PET, polyester, polyolefin copolymer) and any combination thereof.

30. The catheter assembly of claim 1 further comprising a distal hub, the distal hub fixedly engaged to the catheter shaft distal of the distal collar.

31. The catheter assembly of claim 1 further comprising a proximal hub, the proximal hub fixedly engaged to the catheter shaft proximal of the proximal collar.

32. The catheter assembly of claim 1 further comprising a secondary guidewire housing, the secondary guidewire housing comprising a substantially tubular member engaged to the balloon, the secondary guidewire housing defining a secondary guidewire lumen through which a secondary guidewire may be slidingly positioned.

33. The catheter assembly of claim 32 wherein the secondary guidewire housing is at least partially constructed of at least one material of the group consisting of: metal, polymer, natural rubber, silicone, urethanes, Pebax, HDPE, and any combination thereof.

34. The catheter assembly of claim 32 wherein the secondary guidewire housing is integral with the balloon.

35. The catheter assembly of claim 32 wherein the secondary guidewire housing is engaged to an external surface of the balloon.

36. The catheter assembly of claim 35 wherein the secondary guidewire housing is welded to the external surface of the balloon.

37. The catheter assembly of claim 32 wherein the secondary guidewire housing extends from a proximal end of the balloon body to an intermediate region of the balloon body.

38. The catheter assembly of claim 32 wherein the secondary guidewire has a length at least as long as the balloon body.

39. The catheter assembly of claim 32 further comprising a balloon expandable stent, the stent being expandable from an unexpanded configuration to and expanded configuration, in the unexpanded configuration the stent being disposed about at least a portion of the balloon body.

40. The catheter assembly of claim 39 wherein at least a proximal portion of the stent overlays at least a portion of the secondary guidewire housing.

41. The catheter assembly of claim 40 wherein the stent comprises a plurality of interconnected members, wherein adjacent members define openings there between, one of the openings being a secondary opening through which the secondary guidewire radially extends.

42. The catheter assembly of claim 41 wherein a distal end of the secondary guidewire housing extends radially through the secondary opening.

43. The catheter assembly of claim 39 wherein at least a portion of the stent is coated with at least one therapeutic agent.

44. The catheter assembly of claim 43 wherein the at least one therapeutic agent is at least one non-genetic therapeutic agent selected from at least one member of the group consisting of: anti-thrombogenic agents; anti-pro liferative agents; anti-inflammatory agents; antineoplastic/antiproliferative/ anti-miotic agents; anesthetic agents including lidocaine, bupivacaine and ropivacaine; anti-coagulants; vascular cell growth promoters; vascular cell growth inhibitors; bifunctional molecules consisting of an antibody and a cytotoxin; cholesterol-lowering agents; vasodilating agents; and agents which interfere with endogenous vascoactive mechanisms, and any combinations thereof.

45. The catheter assembly of claim 44, wherein the non-genetic therapeutic agent is an anti-thrombogenic agent selected from at least one member of the group consisting of: heparin, heparin derivatives, urokinase, and PPack (dextrophenylalanine proline arginine chloromethylketone).

46. The catheter assembly of claim 44, wherein the non-genetic therapeutic agent is anti-proliferative agent selected from at least one member of the group consisting of: enoxaprin, angiopeptin, monoclonal antibodies capable of blocking smooth muscle cell proliferation, hirudin, and acetylsalicylic acid.

47. The catheter assembly of claim 44, wherein the non-genetic therapeutic agent is an anti-inflammatory agents selected from at least one member of the group consisting of: dexamethasone, prednisolone, corticosterone, budesonide, estrogen, sulfasalazine, and mesalamine.

48. The catheter assembly of claim 44, wherein the non-genetic therapeutic agent is selected from at least one member of the group consisting of: paclitaxel, 5-fluorouracil, cisplatin, vinblastine, vincristine, epothilones, endostatin, angiostatin, and thymidine kinase inhibitors.

49. The catheter assembly of claim 44, wherein the non-genetic therapeutic agent is an anti-coagulants selected from at least one member of the group consisting of: D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors, and tick antiplatelet peptides.

50. The catheter assembly of claim 43 wherein the at least one therapeutic agent is at least one genetic therapeutic agent selected from at least one member of the group consisting of: anti-sense DNA and RNA; DNA coding for anti-sense RNA, tRNA or rRNA to replace defective or deficient endogenous molecules; angiogenic factors including growth factors; cell cycle inhibitors including CD inhibitors, thymidine kinase ("TK") and other agents useful for interfering with cell proliferation; at least one of the family of bone morphogenic proteins ("BMP's"); dimeric proteins; molecules capable of inducing an upstream or downstream effect of a BMP, or the DNA's encoding them and any combinations thereof.

51. The catheter assembly of claim 43 wherein the at least one therapeutic agent is at least one type of cellular material selected from at least one member of the group consisting of: cells of human origin (autologous or allogeneic); cells of non-human origin (xenogeneic) and any combination thereof.

52. The catheter assembly of claim 51 wherein the cellular material is selected from at least one member of the group consisting of: side population cells; lineage negative cells; lineage negative CD34" cells; lineage negative CD34$^+$ cells; lineage negative "cKit$^+$cells; mesenchymal stem cells; cord blood bells; cardiac or other tissue derived stem cells; whole bone marrow; bone marrow mononuclear cells; endothelial progenitor cells; satellite cells; muscle derived cells; go cells; endothelial cells; adult cardiomyocytes; fibroblasts; smooth muscle cells; cultures of mesenchymal stem cells with 5-aza forces differentiation into cardiomyocytes; adult cardiac fibroblasts+5-aza; genetically modified cells; tissue engineered grafts; MyoD scar fibroblasts; Pacing cells; embryonic stem cell clones; embryonic stem cells; fetal or neonatal cells; immunologically masked cells; tissue engineered grafts; genetically modified cells; teratoma derived cells and any combinations thereof.

53. The catheter assembly of claim 43 wherein the at least one therapeutic agent comprises at least one polymer coating, the at least one coating selected from at least one member of the group consisting of: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers; polyvinyl ethers; polyvinyl aromatics; polyethylene oxides; glycosaminoglycans; polysaccharides; polyethylene terephthalate; polyacrylamides; polyethers; polyether sulfone; polycarbonate; polypropylene; polyethylene; and high molecular weight polyethylene; polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions; polysaccharides; hyaluronic acid; squalene emulsions; polyacrylic acid, a copolymer of polylactic acid and polycaprolactone; PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/P0$^{4+}$'s; cyanoacrylate; 50/50 DLPLG; polydioxanone; polypropylene fumarate; polydepsipeptides; chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; A block copolymers; B block copolymers and any combinations thereof.

54. A catheter assembly comprising:
a catheter shaft, the catheter shaft having a length and an outer surface;
a balloon disposed about at least a portion of the outer surface of the catheter shaft, the balloon comprising a proximal balloon waist, a distal balloon waist and a body portion there between, the balloon having an expanded state and a unexpanded state, in the expanded state the body portion having an expanded diameter and in the unexpanded state the body portion having an unexpanded diameter that is less than the expanded diameter; and
one or more collars disposed between the outer surface of the catheter shaft and at least one of the proximal waist and distal waist of the balloon, the one or more collars including an electroactive polymer material having a contracted state and an expanded state, wherein the balloon is rotatable relative to the catheter shaft when the electroactive polymer material of the one or more collars in the contracted state and the balloon is sealingly engaged to the catheter shaft when the electroactive polymer material of the one or more collars is in the expanded state.

55. The catheter assembly of claim 54, wherein the electroactive polymer material of the one or more collars is electrically actuatable between the contracted state and the expanded state.

56. The catheter assembly of claim 54, wherein the one or more collars are fixed to at least one of the proximal waist and the distal waist of the balloon.

57. The catheter assembly of claim 54, wherein the one or more collars are fixed to the catheter shaft.

* * * * *

UNITED STATES PATENT AND TRADEMARK OFFICE
CERTIFICATE OF CORRECTION

PATENT NO. : 7,744,619 B2  Page 1 of 1
APPLICATION NO. : 10/785449
DATED : June 29, 2010
INVENTOR(S) : Tracee Eidenschink It is certified that error appears in the above-identified patent and that said Letters Patent is hereby corrected as shown below:

Column 4
Line 57: delete "is" and insert therefor -- in --.

Column 7
Line 53: delete "grove" and insert therefor -- groove --.
Line 57: delete "grove" and insert therefor -- groove --.

Column 11
Line 63: delete "would" and insert therefor -- wound --.

Column 14
Line 8: delete "x-methylstyrene" and insert therefor -- α-methylstyrene --.

Column 17
Line 46: delete "Nation," and insert therefor -- Nafion®, --.

Signed and Sealed this

Fourteenth Day of September, 2010

David J. Kappos
*Director of the United States Patent and Trademark Office*